(12) United States Patent
Kahn et al.

(10) Patent No.: US 11,013,711 B2
(45) Date of Patent: May 25, 2021

(54) FATTY ACID ESTERS OF HYDROXY FATTY ACIDS (FAHFAS) FOR USE IN THE TREATMENT OF TYPE 1 DIABETES

(71) Applicants: Beth Israel Deaconess Medical Center, Inc., Boston, MA (US); Salk Institute for Biological Studies, La Jolla, CA (US); President and Fellows of Harvard College, Cambridge, MA (US)

(72) Inventors: Barbara B. Kahn, Cambridge, MA (US); Alan Saghatelian, La Jolla, CA (US); Ismail Syed, Revere, MA (US)

(73) Assignees: Beth Israel Deaconess Medical Center, Inc., Boston, MA (US); Salk Institute for Biological Studies, La Jolla, CA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/308,597

(22) PCT Filed: Jun. 9, 2017

(86) PCT No.: PCT/US2017/036789
§ 371 (c)(1),
(2) Date: Dec. 10, 2018

(87) PCT Pub. No.: WO2017/214527
PCT Pub. Date: Dec. 14, 2017

(65) Prior Publication Data
US 2019/0151276 A1   May 23, 2019

Related U.S. Application Data

(60) Provisional application No. 62/348,591, filed on Jun. 10, 2016.

(51) Int. Cl.
*A61K 31/23* (2006.01)
*A61K 31/22* (2006.01)
*A61P 3/10* (2006.01)

(52) U.S. Cl.
CPC .............. *A61K 31/23* (2013.01); *A61K 31/22* (2013.01); *A61P 3/10* (2018.01)

(58) Field of Classification Search
CPC .................................................... A61K 31/23
See application file for complete search history.

(56) References Cited

U.S. PATENT DOCUMENTS

| | | | |
|---|---|---|---|
| 4,629,736 A | 12/1986 | Tsukamoto et al. | |
| 4,639,369 A | 1/1987 | Ciaudelli | |
| 5,362,878 A | 11/1994 | Chang et al. | |
| 5,780,237 A | 7/1998 | Bursten | |
| 5,993,861 A | 11/1999 | Fogel | |
| 6,290,973 B1 | 9/2001 | Hawkins et al. | |
| 10,604,473 B2 | 3/2020 | Kahn et al. | |
| 2007/0092475 A1 | 4/2007 | Wohlman | |
| 2008/0015227 A1 | 1/2008 | Kym | |
| 2015/0133551 A1 | 5/2015 | Kahn et al. | |
| 2016/0221925 A1 | 8/2016 | Kahn et al. | |
| 2018/0194714 A1 | 7/2018 | Kahn et al. | |

FOREIGN PATENT DOCUMENTS

| | | | | |
|---|---|---|---|---|
| JP | 2000-226397 A | 8/2000 | | |
| JP | 2001-270851 A | 10/2001 | | |
| WO | WO 1994/006014 A | 8/2000 | | |
| WO | WO 2004/089869 A1 | 10/2004 | | |
| WO | 2006117668 A1 | 11/2006 | | |
| WO | WO 2008/059035 A2 | 5/2008 | | |
| WO | WO 2013/166431 A1 | 11/2013 | | |
| WO | WO-2013166431 A1 * | 11/2013 | ............. | C07C 69/24 |
| WO | WO 2014/144777 A2 | 9/2014 | | |
| WO | WO-2014144777 A2 * | 9/2014 | ............. | G01N 33/92 |
| WO | WO 2017/070515 A2 | 4/2017 | | |
| WO | WO 2017/214527 A1 | 12/2017 | | |

OTHER PUBLICATIONS

Lundh et al., Histone deacetylases 1 and 3 but not 2 mediate cytokine-induced beta cell apoptosis in INS-1 cells and dispersed primary islets from rats and are differentially regulated in the islets of type 1 diabetic children, Diabetologia; Heidelberg vol. 55, Iss. 9, (Sep. 2012): 2421-31.*
Yore et al., Discovery of a Class of Endogenous Mammalian Lipids with Anti-Diabetic and Anti-inflammatory Effects, Cell, Cell Press, US, vol. 159, No. 2, Oct. 9, 2014 (Oct. 9, 2014), pp. 318-332.*
Osborne, Type 1 and Type 2 Diabetes: What's the Difference?, Jan. 14, 2019, available at https://www.healthline.com/health/difference-between-type-1-and-type-2-diabetes#treatnnent.*
Advisory Action for U.S. Appl. No. 14/775,399, entitled: "Lipids That Increase Insulin Sensitivity and Methods of Using the Same," dated Sep. 21, 2018.
Amspacher, D.R. et al., "Synthesis of a Reaction Intermediate Analogue of Biotin-Dependent Carboxylases via a Selective Derivatization of Biotin," Organic Letters 1(1):99-102 (1999).
Applewhite, T.H. et al., "Optical Rotatory Dispersion and Absolute Configuration of Some Long-Chain Hydroxy Acids," Journal of Organic Chemistry, vol. 32; No. 4; 1173-1178 (1967).
Bocan, T.M.A. et al., "Comparison of CI-976, An Acat Inhibitor, and Selected Lipid-Lowering Agents for Antiatherosclerotic Activity in Iliac-Femoral and Thoracic Aortic Lesions A Biomedical, Morphological, and Morphometric Evaluation," American Heart Association 11(34):1830-1843 (1991).
Boga, C. et al., "Fluorescein conjugates of 90 and 10-hydroxystearic acids: synthetic strategies, photophysical characterization, and confocal microscopy applications," Analytical Biochemistry, Academic Press 335(2):196-209 (2004).

(Continued)

*Primary Examiner* — Svetlana M Ivanova
(74) *Attorney, Agent, or Firm* — Hamilton, Brook, Smith & Reynolds, P.C.

(57) ABSTRACT

Provided herein are methods for treating type 1 diabetes and its sequelae (e.g., cardiovascular, renal or neurologic diseases for which type 1 diabetes is a risk factor) in a subject in need thereof, comprising administering to the subject a therapeutically effective amount of a fatty acid ester of a hydroxy fatty acid (FAHFA), or a pharmaceutically acceptable salt thereof.

11 Claims, 18 Drawing Sheets

(56) References Cited

OTHER PUBLICATIONS

Brezinova, M. et al., "Levels of palmitic acid ester of hydroxystearic acid (PAHSA) are reduced in the breast milk of obese mothers," BBA—Molecular and Cell Biology of Lipids; vol. 1863; No. 2; 126-131 (2018).
Charron, G. et al., "Robust Fluorescent Detection of Protein Fatty-Acylation with Chemical Reporters," Journal of the American Chemical Society 131(13):4967-4975 (2009).
Dignass, A.U. et al., "Review article: the aetiopathogenesis of inflammatory bowel disease—immunology and repair mechanisms," Aliment Pharmacol. Ther., vol. 20; Suppl. 4; 9-17 (2004).
Final Office Action for U.S. Appl. No. 14/398,198, "Lipids That Increase Insulin Sensitivity and Methods of Using the Same", dated Nov. 22, 2016.
Final Office Action for U.S. Appl. No. 14/775,399, "Lipids That Increase Insulin Sensitivity and Methods of Using the Same,", dated Apr. 23, 2018.
Gersemann, M. et al., "Innate immune dysfunction in inflammatory bowel disease," Journal of Internal Medicine, vol. 271; 421-428 (2012).
Gu., W. and Gin, D.L., "Aromatic Side Chain-Functionalized Long Chain Acid Salts: Structural Factors Influencing Their Lyotropic Liquid-Crystalline Behavior," Langmuir, vol. 18: 7415-7427 (2002).
Harlan Laboratories: Teklad 6% Fat Mouse/Rat diet,: 2008, XP002703263, Retrieved from the Internet: URL:http://www.harlan.com/products_and_services/research_models_and_services/laboratory_animal_diets/teklad_natural_ingredient_diets/teklad_traditional_diets/rodent_diets/teklad_6_mouse_rat_diet_002.hl [Retrieved on Jul. 17, 2013].
Harry-Okuru, R.E. et al., "Synthesis of estolide esters from cis-9-octadecenoic acid estolides," Journal of the American Oil Chemists 78(3): 219-222 (2001).
Hediger, M.L., "Association Between Infant Breastfeeding and Overweight in Young Children," JAMA, vol. 285; 2453-2460 (2001).
Homan, E., "Discovery of Novel Lipid Pathways Associated with the Metabolic Syndrome," Retrieved from Internet URL: http:/dash.hardvard.edu/handle/1/10310131?show=full [Retrieved Aug. 24, 2014].
Homan, E., "Discovery of Novel Lipid Pathways Associated with the Metabolic Syndrome," ProQuest, UMI Dissertations Publishing (May 3, 2012), Retrieved from the internet: URL: http://search.proquest.com/pqdtscieng/docview/1028547458/335A06-2FEA03425FPQ/1?accountid=29404 [retrieved on Aug. 8, 2014].
Iizuka, K. et al., "Deficiency of carbohydrate-activated transcription factor ChREBP presents obesity and improves plasma glucose control in leptin-deficient (ob/ob) mice," Endocrinology and Metabolism 291(2):E358-E364 (2006).
Jiang, Z. et al., "Lipid A Structures Containing Novel Lipid Moieties: Synthesis and Adjuvant Properties,"Bioorganice & Medicinal Chemistry Letters, vol. 12: 2193-2196 (2002).
King, A.J. et al., "Diacylglycerol Acyltransferase 1 Inhibition Lowers Serum Triglycerides in the Zucker Fatty Rat and the Hyperlipidemic Hamster," Journal of Pharmacology and Experimental Therapeutics, 330(2): 526-531 (2009).
Landham, R. R. et al., ""Organotitanate dispersants for BaTiOa and Alz03"", Journal of Materials Science, Jan. 1, 1987, p. 1681,XP055371293.
Nakamura, T. et al., "Synthesis of Carboxymethyl GLA-60 Ether Derivatives Containing an Olefin in Their Chains and Their LPS-Antagonisitc Activities", Bull. Chem. Soc. Jpn., vol. 76: 1011-1022 (2003).
New Class of Good Fats Offers a Promising Direction for Diabetes Prevention, Treatment, Retrieved from the Internet URL: http://www.bidmc.org [retreived on Jul. 28, 2017].
Non-Final Office Action for U.S. Appl. No. 14/398,198, "Lipids That Increase Insulin Sensitivity and Methods of Using the Same", dated Feb. 19, 2016.
Non-Final Office Action for U.S. Appl. No. 14/775,399, "Lipids That Increase Insulin Sensitivity and Methods of Using the Same,", dated Apr. 28, 2017.
Non-Final Office Action for U.S. Appl. No. 14/398,198, "Lipids That Increase Insulin Sensitivity and Methods of Using the Same", dated Sep. 8, 2017.
Non-Final Office Action for U.S. Appl. No. 15/915,957, "Lipids That Increase Insulin Sensitivity and Methods of Using the Same", dated Nov. 25, 2019.
Non Final Office Action for U.S. Appl. No. 14/775,399, entitled: "Lipids That Increase Insulin Sensitivity and Methods of Using the Same," dated Feb. 8, 2019.
Notification of Transmittal of the International Search Report and Written Opinion for International Application No. PCT/US2013/039532, entitled, "Lipids That Increase Insulin Sensitivity and Methods of Using the Same", dated Aug. 2, 2013.
Notification of Transmittal of the International Search Report and Written Opinion for International Application No. PCT/US2014/029329, entitled, "Lipids That Increase Insulin Sensitivity and Methods of Using the Same", dated Sep. 30, 2014.
Notification Concerning Transmittal of International Preliminary Report on Patentability (IPRP) and accompanying IPRP and Written Opinion, International Application No. PCT/US2013/039532, entitled "Lipids That Increase Insulin Sensitivity and Methods of Using the Same", dated Nov. 13, 2014.
Notification Concerning Transmittal of International Preliminary Report on Patentability (IPRP) and accompanying IPRP and Written Opinion, International Application No. PCT/US2014/029329, entitled "Lipids That Increase Insulin Sensitivity and Methods of Using the Same", dated Sep. 24, 2015.
Notification of Transmittal of the International Search Report and Written Opinion for International Application No. PCT/US2016/058184, entitled, "Methods of Preventing and Treating Inflammatory Bowel Disease With Branched Fatty Acid Esters of Hydroxy Fatty Acids (FAHFAS)", dated Apr. 18, 2017.
Notification of Transmittal of the International Search Report and Written Opinion for International Application No. PCT/US2017/036789, entitled, "Fatty Acid Esters of Hydroxy Fatty Acids (FAHFAs) for Use in the Treatment of Type 1 Diabetes", dated Aug. 21, 2017.
Notification Concerning Transmittal of International Preliminary Report on Patentability (IPRP) and accompanying IPRP and Written Opinion, International Application No. PCT/US2016/058184, entitled, "Methods of Preventing and Treating Inflammatory Bowel Disease With Branched Fatty Acid Esters of Hydroxy Fatty Acids (FAHFAS)", dated May 3, 2018.
Notification Concerning Transmittal of International Preliminary Report on Patentability for International Application No. PCT/US2017/036789, entitled, "Fatty Acid Esters of Hydroxy Fatty Acids (FAHFAs) for Use in the Treatment of Type 1 Diabetes," dated Dec. 20, 2018.
Notice of Allowance for U.S. Appl. No. 14/775,399, "Lipids That Increase Insulin Sensitivity and Methods of Using the Same," dated Nov. 22, 2019.
Padgett, L.E., et al., "Loss of NADPH Oxidase-Derived Supoeroxide Skews Macrophage Phenotypes to Delay Type 1 Diabetes," Diabetes, 64:937-946 (2015).
Pastorelli, L. et al., "Central role of the gut epithelian barrier in the pathogenesis of chronic intestinal inflammation: lessons learned from animal models and human genetics," Frontiers in Immunology, vol. 4; Article 280; 1-22 (2013).
Saghatelian, A., "Discovery of Novel Lipid Pathways Associated with the Metabolic Syndrome," Digital Access to Scholarship at Harvard (DASH) (Feb. 19, 2013), Retrieved from the internet: URL: http://dash.harvard.edu.handle/1/10310131?show=full [retrieved on Aug. 28, 2014].
Shimoyama, A. et al., "Chemical Synthesis of Helicobacter pylori Lipopolysaccharide Partial Structures and their Selective Proinflammatory Responses," Dec. 16, 2011; first published Nov. 16, 2011; Chem. Eur. J. 17: 14464-14474 & Supplemental section, pp. 1-39.
Weber, N. et al., "Antioxidants eliminate stereomutation and thioether formation during lipase-catalyzed thioesterification and

(56) References Cited

OTHER PUBLICATIONS transthioesterification for the preparation of uniform cis- and trans-unsaturated thioesters," Chemistry and Physics of Lipids, vol. 105: 215-233 (2000).

Yore, M. M. et al., "Discovery of a Class of Endogenous Mammalian Lipids with Anti-Diabetic and Anti-inflammatory Effects," Cell, vol. 159: 318-332 (2014).

Kuda, O., "On the Complexity of PAHSA Research," Cell Metabolism, vol. 28; 541-542 (2018).

Pflimlin, E. et al., "Acute and Repeated Treatment with 5-PAHSA or 9-PAHSA Isomers Does Not Improve Glucose Control in Mice," Cell Metabolism, vol. 28; 217-227 (2018).

Syed, I. et al., "Methodological issues in Studying PAHSA Biology: Masking PAHSA Effects, Supplemental Information" Cell Metab., vol. 28; No. 4; 543-546 (2018).

Syed, I. et al., "Methodological Issues in Studying PAHSA Biology: Masking PAHSA Effects," HHS Public Access, Cell Metab, Author manuscript, May 30, 2019.

Syed, I. et al., "Methodological Issues in Studying PAHSA Biology: Masking PAHSA Effects," Cell Metab., vol. 28; No. 4; 543-546 (2018).

Final Office Action for U.S. Appl. No. 15/915,957, dated Sep. 3, 2020.

\* cited by examiner

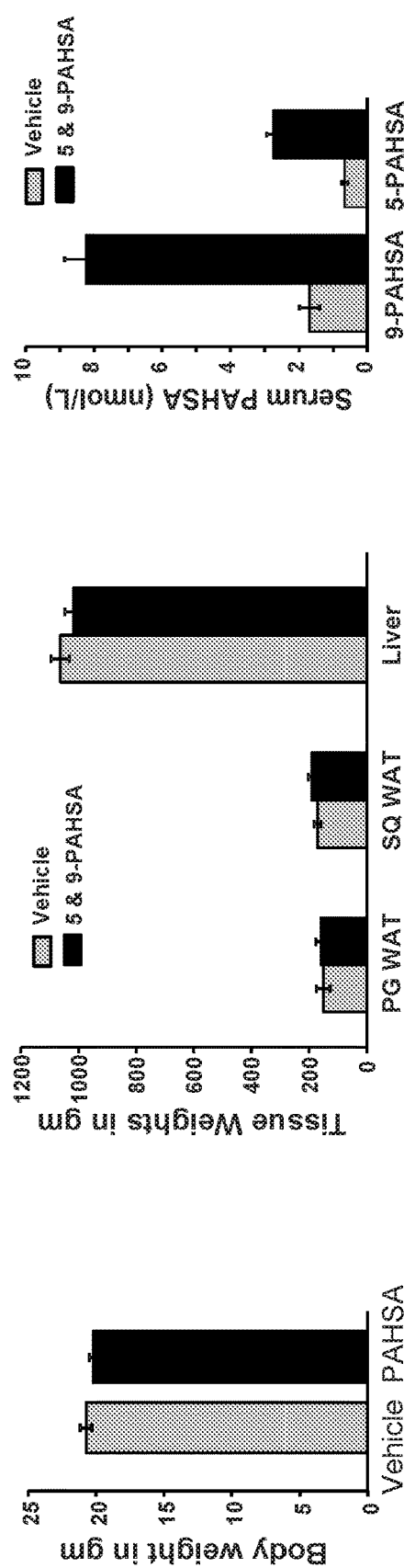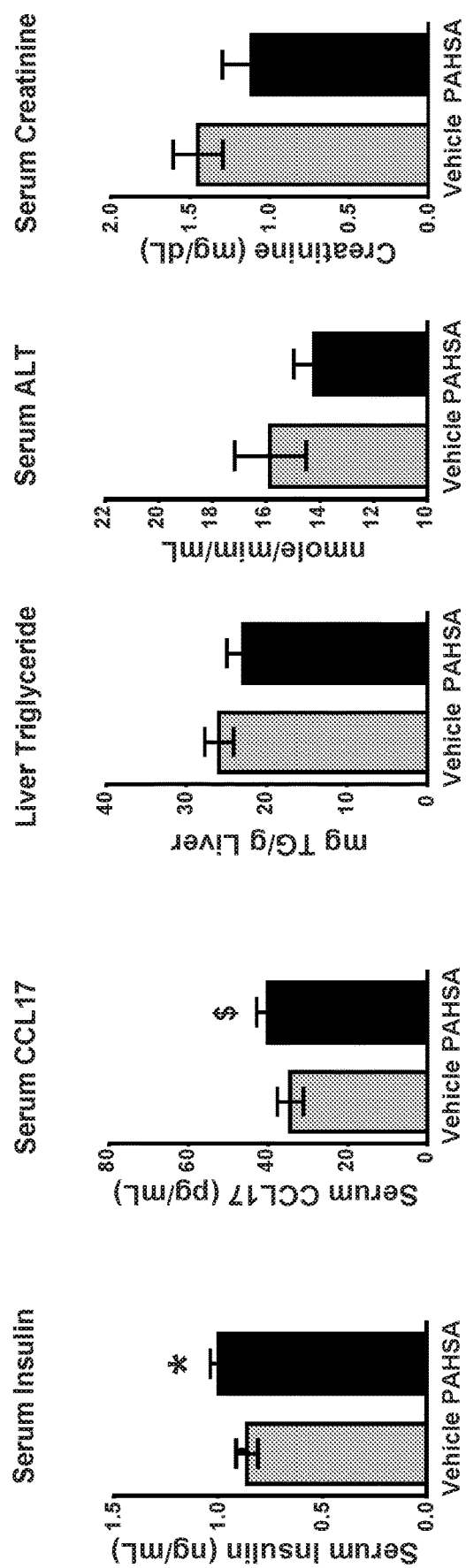
FIG. 1A
FIG. 1B
FIG. 1C
FIG. 1D
FIG. 1E
FIG. 1F

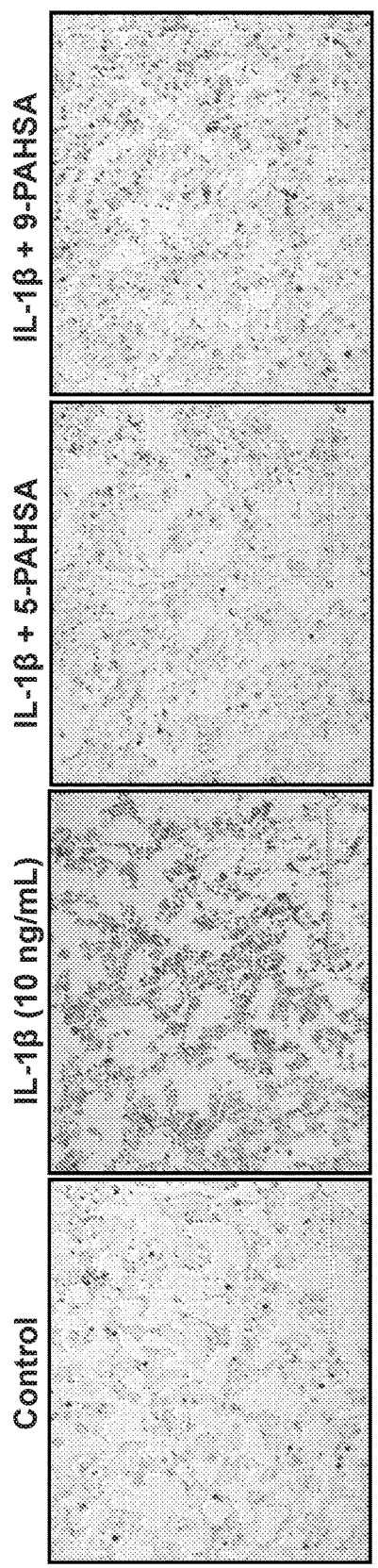
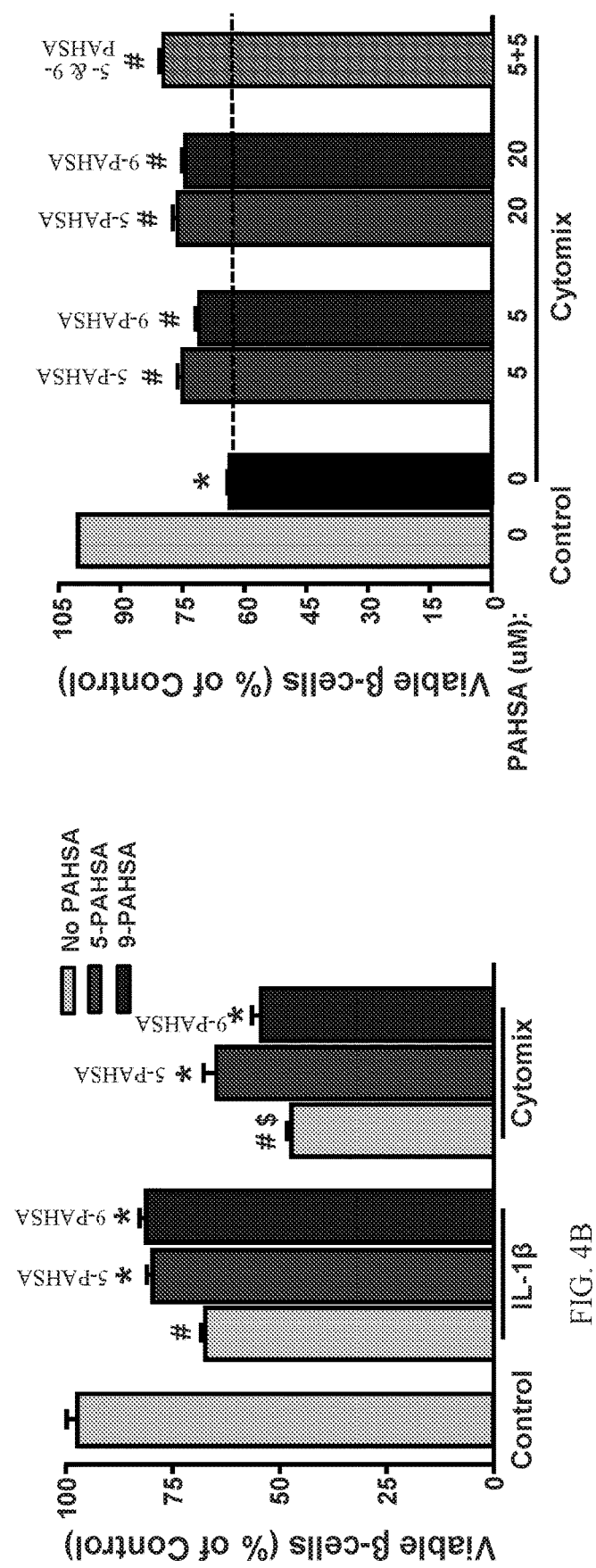
FIG. 4A
FIG. 4B
FIG. 4C

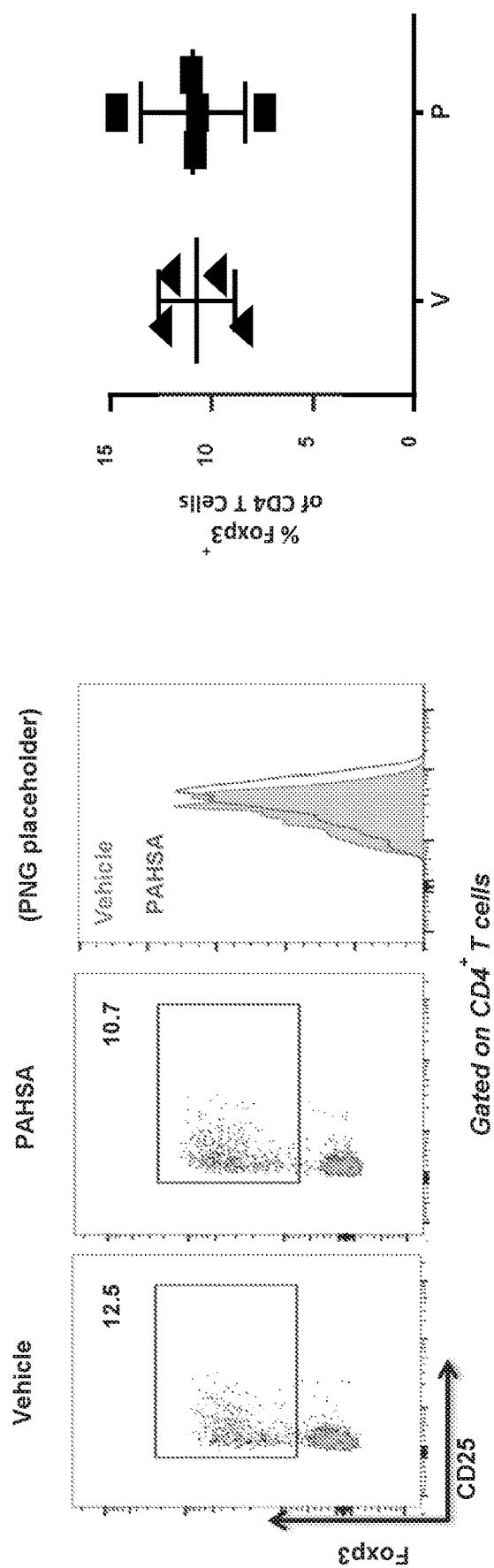
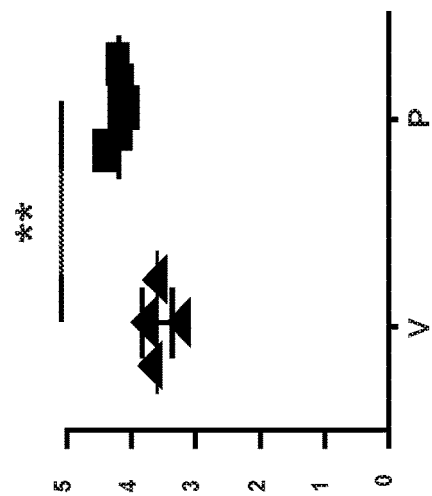
FIG. 9D
FIG. 9E

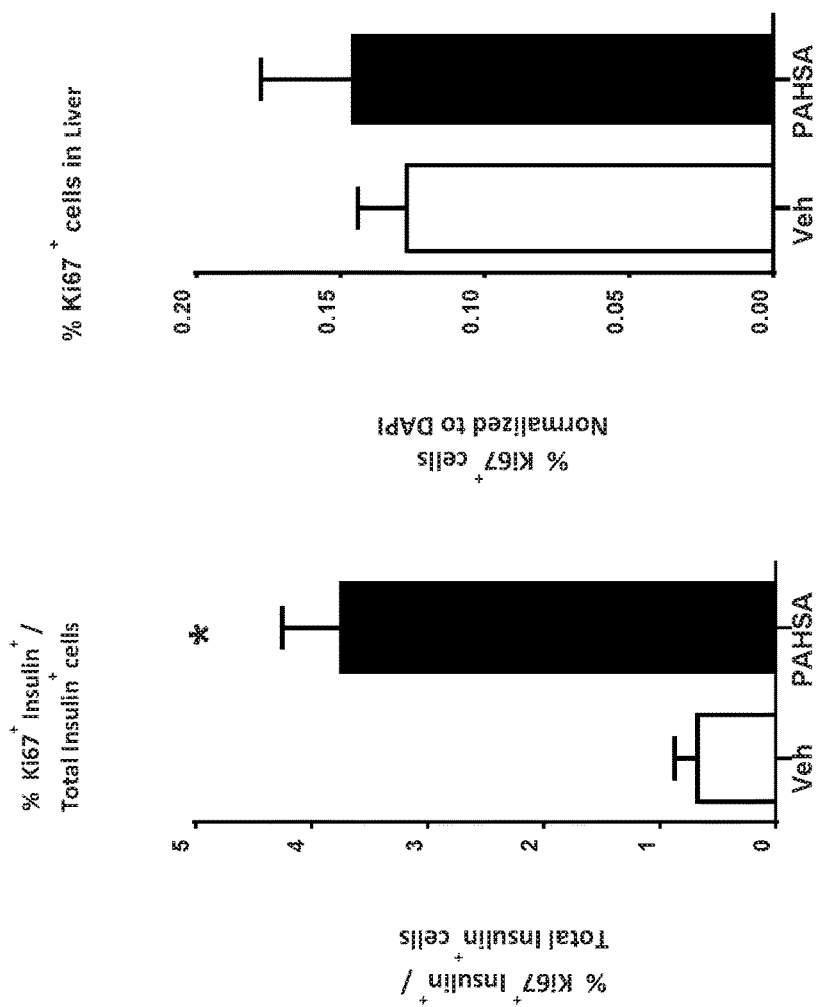
FIG. 11D
FIG. 11C
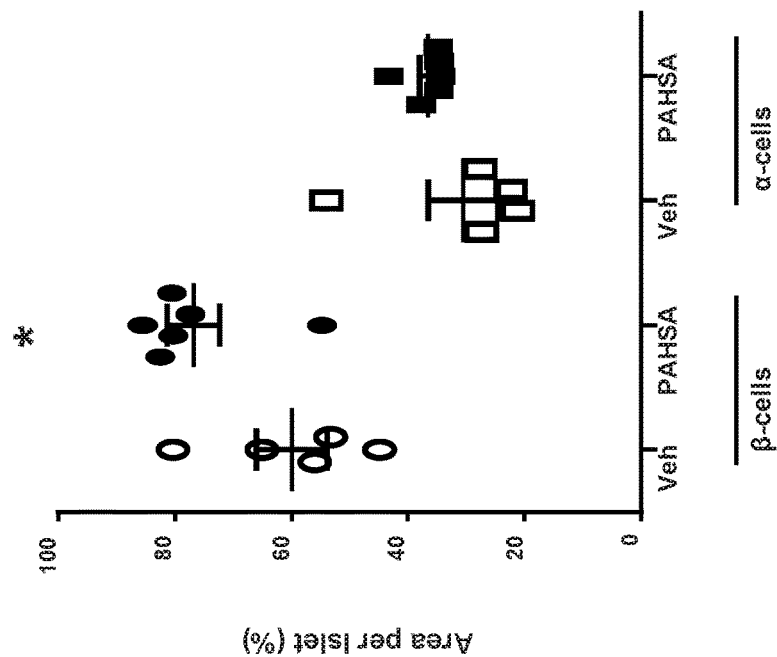
FIG. 11B

@ p<0.05 vs control 2.5 mM glucose
* p<0.05 vs respective 2.5 mM glucose
$ p<0.05 vs Control 20 mM glucose
# p<0.05 vs Control and Cytomix 20 mM glucose

FATTY ACID ESTERS OF HYDROXY FATTY ACIDS (FAHFAS) FOR USE IN THE TREATMENT OF TYPE 1 DIABETES

RELATED APPLICATION

This application is the U.S. National Stage of International Application No. PCT/US2017/036789, filed on Jun. 9, 2017, which designates the U.S., published in English, and claims the benefit of U.S. Provisional Application No. 62/348,591, filed on Jun. 10, 2016. The entire teachings of these applications are incorporated herein by reference.

GOVERNMENT SUPPORT

The invention was made with government support under grant DK098002 awarded by the National Institutes of Heath (NIH). The government has certain rights in the invention.

BACKGROUND

The standard of care for type 1 diabetes (T1D) involves following a strict diet and exercise regimen in conjunction with insulin injections multiple times a day or insulin pump therapy. Type 1 diabetic patients need to measure their blood sugar many times a day and take carbohydrate if their blood sugar level is low or insulin if their blood sugar level is high. In addition, type 1 diabetic patients are at risk for severe complications including blindness, kidney failure, neuropathy, cardiovascular disease and limb amputations from relentless infections. Even with the best treatment regimens, life expectancy is reduced in people with type 1 diabetes. Preventing or even delaying the onset of type 1 diabetes or reducing its severity would be major advances for type 1 diabetes.

Accordingly, there is a need for safe and well-tolerated treatment regimens that can prevent, delay or treat type 1 diabetes and its associated complications.

SUMMARY OF THE INVENTION

Provided herein are methods for treating type 1 diabetes and its sequelae (e.g., cardiovascular, renal or neurologic diseases for which type 1 diabetes is a risk factor) with fatty acid esters of hydroxy fatty acids (FAHFAs) or their pharmaceutically acceptable salts.

One embodiment is a method for treating type 1 diabetes in a subject in need thereof, comprising administering to the subject a therapeutically or prophylactically (e.g., therapeutically) effective amount of a FAHFA, or a pharmaceutically acceptable salt thereof.

Another embodiment is a method for treating one or more sequelae of type 1 diabetes in a subject in need thereof, comprising administering to the subject a therapeutically or prophylactically (e.g., therapeutically) effective amount of a FAHFA, or a pharmaceutically acceptable salt thereof.

Another embodiment is a method for inhibiting cytokine-induced apoptosis or necrosis of a β-cell, promoting islet viability of a β-cell or stimulating proliferation of a β-cell, comprising contacting the β-cell with a FAHFA, or a pharmaceutically acceptable salt thereof.

Yet another embodiment is a method for treating insulitis in a subject in need thereof, comprising administering to the subject a therapeutically or prophylactically (e.g., therapeutically) effective amount of a FAHFA, or a pharmaceutically acceptable salt thereof.

Yet another embodiment is a method for inhibiting caspase-3 degradation or cleavage of poly(ADP-ribose) polymerase (PARP) in a cell, comprising contacting the cell with a FAHFA, or a pharmaceutically acceptable salt thereof.

Yet another embodiment is a method for inhibiting cell death induced by endoplasmic reticulum stress, comprising contacting a cell with a FAHFA, or a pharmaceutically acceptable salt thereof.

Yet another embodiment is a method for inhibiting leukocyte infiltration or T-cell activation, comprising administering to a subject a therapeutically or prophylactically (e.g., therapeutically) effective amount of a FAHFA, or a pharmaceutically acceptable salt thereof.

Yet another embodiment is a method for stimulating insulin secretion (e.g., stimulating glucose-stimulated insulin secretion (GSIS)) in a cell, comprising administering to the cell a FAHFA, or a pharmaceutically acceptable salt thereof.

Also provided herein is use of a FAHFA, or a pharmaceutically acceptable salt thereof, for the manufacture of a medicament for treating type 1 diabetes; a FAHFA, or a pharmaceutically acceptable salt thereof, for use in the treatment of type 1 diabetes; and a pharmaceutical composition for treating type 1 diabetes, comprising a FAHFA, or a pharmaceutically acceptable salt thereof.

FAHFAs are inexpensive to make and represent a potentially safe and well-tolerated approach to treating type 1 diabetes and its sequelae because FAHFAs are naturally found in the human body and in human diet (e.g., dairy, meat, vegetables). The in vitro data disclosed herein show that more than one FAHFA can attenuate cytokine-induced β-cell apoptosis (by between about 50% and about 75%) and necrosis (by about 75%) and improve β-cell viability. In addition, FAHFAs augment islet β-cell proliferation and potentiate glucose-stimulated insulin secretion under the duress of cytokines. In in vivo experiments, FAHFA-treated non-obese diabetic (NOD) mice (an autoimmune model for type 1 diabetes) showed low and delayed incidence of type 1 diabetes compared to vehicle-treated mice (8 out of 23 FAHFA-treated mice became diabetic compared to 18 out of 21 vehicle-treated mice). In addition, oral FAHFA treatment of NOD mice improved survival rate by 63% over vehicle treatment (3 out of 23 FAHFA-treated mice died compared to 16 out of 21 vehicle-treated mice). Analysis of the innate immune system also revealed elevated levels of CCL17 (also known as thymus- and activation-regulated chemokine (TARC)), a chemokine involved in recruitment of islet protective Th2 cells in FAHFA-treated NOD mice (vehicle 29±4 pg/ml versus FAHFA 37±3 pg/ml).

BRIEF DESCRIPTION OF THE FIGURES

The foregoing will be apparent from the following more particular description of example embodiments of the invention, as illustrated in the accompanying figures.

FIGS. 1A-1F show that chronic 5- and 9-PAHSA treatment augments serum insulin and CCL17 chemokine levels and elevates serum 5- and 9-PAHSA levels in female NOD mice without altering body weight. Body weight (FIG. 1A) and tissue weights (FIG. 1B) in female non-obese diabetic mice treated with 5- and 9-PAHSAs (15 mg/kg body weight per day of each) via oral gavage for 6 weeks (PG WAT: prostaglandin white adipose tissue; SQ WAT: subcutaneous white adipose tissue; n=11-12 mice/group). 5- and 9-PAHSA levels in sera at 6 weeks of 5- and 9-PAHSA treatment (FIG. 1C; n=5-6 mice/group). Serum insulin (FIG.

1D) and CCL17 chemokine (FIG. 1E) levels in vehicle and PAHSA treated mice at ad libitum (n=11-12 mice/group; *: p<0.05; $: p=0.08 versus vehicle treatment). Liver triglycerides and serum ALT and creatinine levels in vehicle and PAHSA treated mice (FIG. 1F; n=5-6 mice/group; data are means±standard error of measurement (SEM)).

Figure 2B:
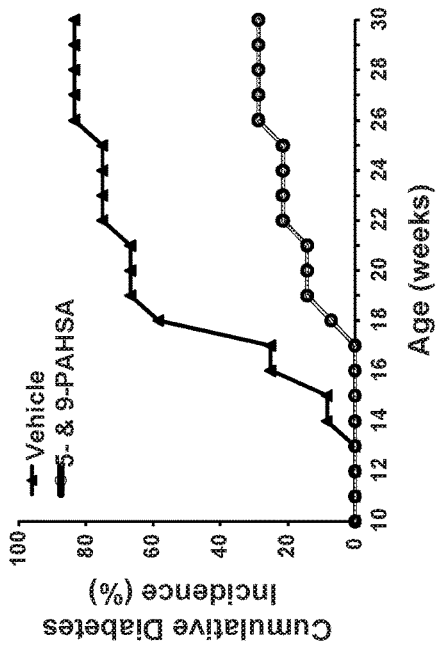
Figure 2A:
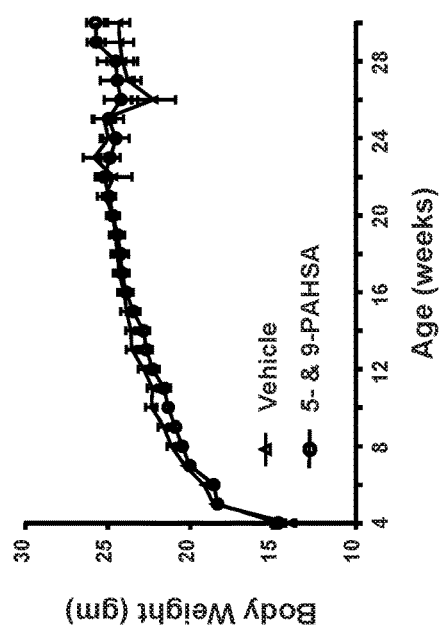
Figure 2E:
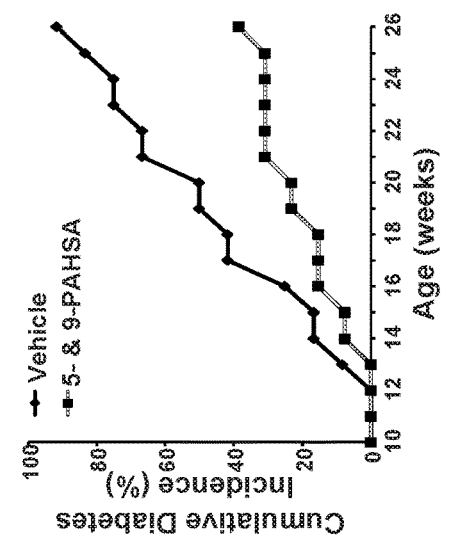
Figure 2D:
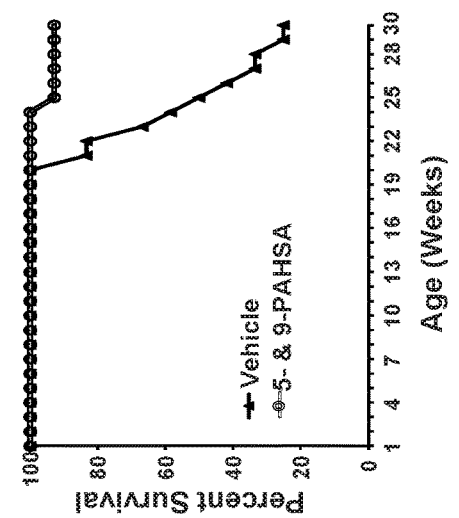
Figure 2C:
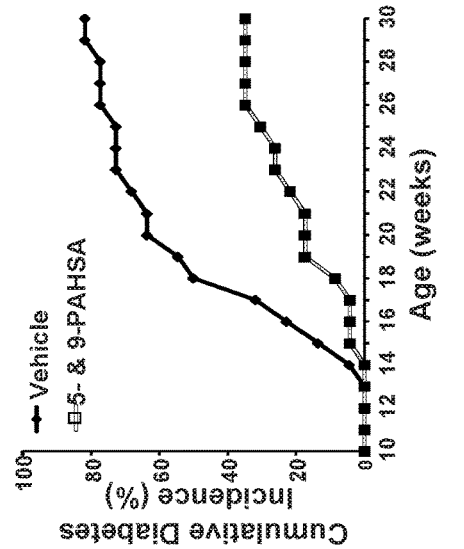

FIGS. 2A-2E show that chronic 5- and 9-PAHSA treatment attenuates percent cumulative diabetes incidence and improves percent survival in female NOD mice. Body weight in female NOD mice treated with vehicle or 5- and 9-PAHSAs (15 mg/kg body weight per day of each) via oral gavage for 26 weeks (FIG. 2A; n=13-14 mice/group; data are means±SEM). Female NOD mice were treated with vehicle and 5- and 9-PAHSA for 26 weeks starting from 4 weeks of age to assess percent cumulative diabetes incidence (FIG. 2B; n=13-14 mice/group) (FIG. 2C; n=22-23 mice/group). Female NOD mice were treated with vehicle or 5- and 9-PAHSA for 26 weeks starting from 4 weeks of age to assess percent survival (FIG. 2D; n=13-14 mice/group). Female NOD mice were treated with vehicle or 5- and 9-PAHSA for 13 weeks starting from 13 weeks of age (late intervention study) to assess percent cumulative diabetes incidence (FIG. 2E; n=13 mice/group).

Figure 3B:
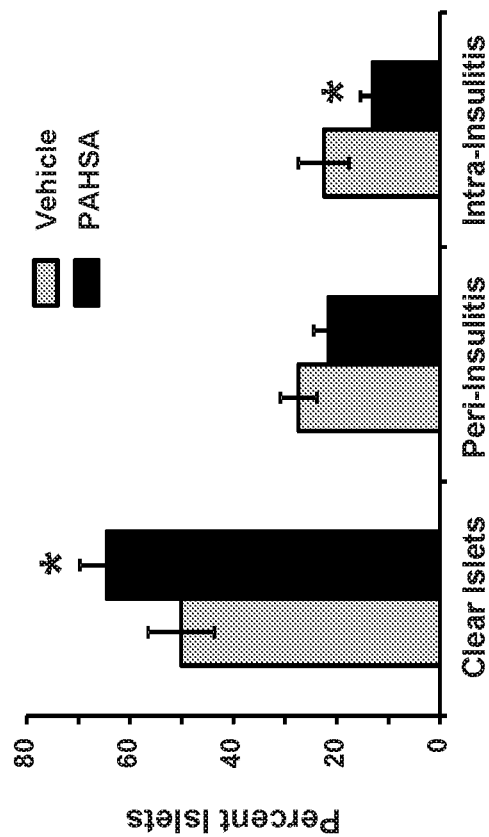
Figure 3A:
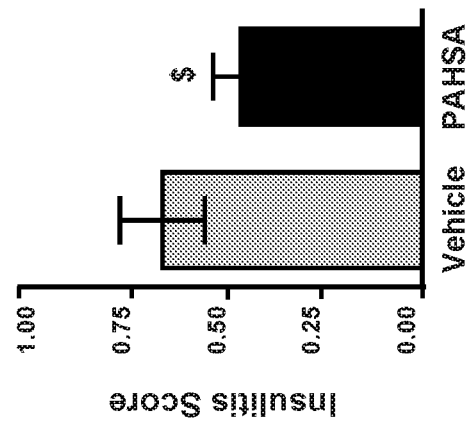

FIGS. 3A and 3B show that chronic 5- and 9-PAHSA treatment attenuates insulitis score and percent intra-insulitis islets in female NOD mice. Female NOD mice were treated with vehicle or 5- and 9-PAHSA for 6 weeks starting from 4 weeks of age to measure insulitis score (FIG. 3A) and percent intra-insulitis islets (FIG. 3B) (n=16-17 mice/group; *: p<0.05 versus vehicle-treated mice; $: p=0.06 versus vehicle-treated mice; data are means±SEM).

FIGS. 4A-4C show that PAHSAs augment percent viable β-cells under cytokine stress in vitro. MIN6 cells were treated with either diluent alone or interleukin 1β (IL-1β; 10 ng/mL) for 48 hours in the presence or absence of 5-PAHSA (5 μM) or 9-PAHSA (5 μM) (FIG. 4A; data are representative of two independent experiments performed in triplicate; magnification: 20×). MIN6 cells were treated with either diluent alone or IL-1β (10 ng/mL) or Cytomix (TNFα+IL-1β+IFN-γ; 10 ng/mL each) for 40 hours in the presence or absence of 5-PAHSA (5 μM) or 9-PAHSA (5 μM) (FIG. 4B). The percent viable β-cells was measured by MTT assay (n=24 wells/condition; #: p<0.05 versus control; $: p<0.05 versus control and IL-1β; *: p<0.05 versus respective cytokine treatment alone; data are means±SEM). MIN6 cells were treated with either diluent alone or Cytomix (TNFα+IL-1β+IFN-γ; 5+5+10 ng/mL) for 48 hours in the presence or absence of 5-PAHSA (5 or 20 μM) or 9-PAHSA (5 or 20 μM) or 5- and 9-PAHSA (5 μM each) (FIG. 4C). The percent viable β-cells was measured by MTT assay (n=30 wells/condition; *: p<0.05 versus control; #: p<0.05 versus control and Cytomix; data are means±SEM).

Figure 5B:
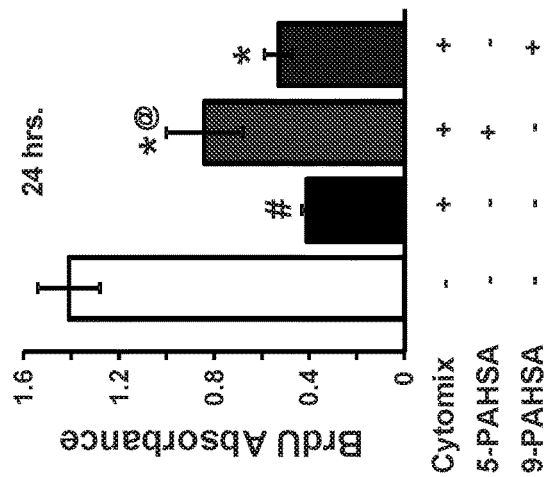
Figure 5C:
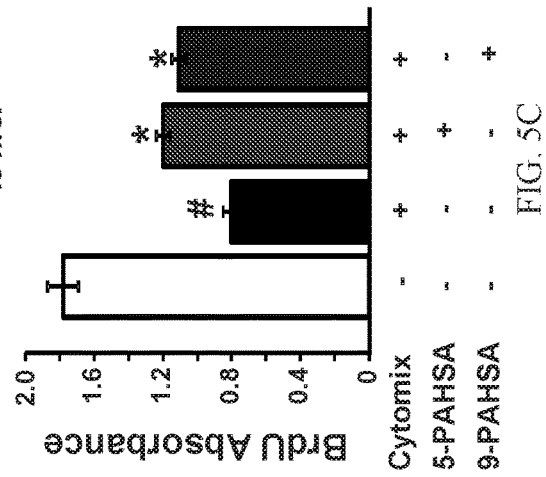
Figure 5A:
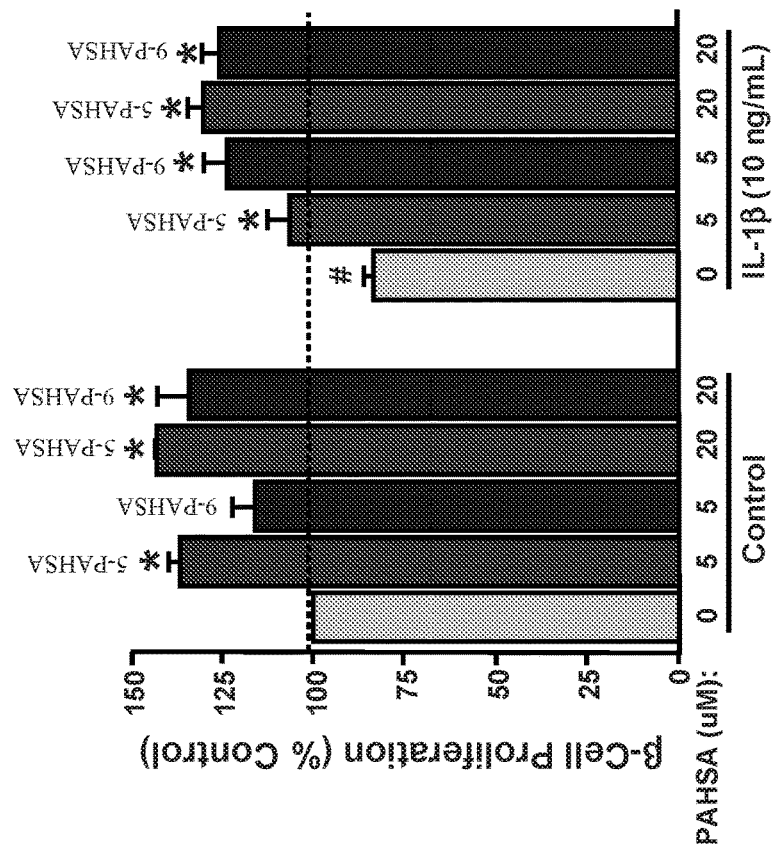

FIGS. 5A-5C show that PAHSAs augment β-cell proliferation during cytokine duress. Cell tracer-tracked MIN6 cells were treated with either diluent alone or IL-1β (10 ng/mL) for 48 hours in the presence or absence of 5-PAHSA (5 and 20 μM) or 9-PAHSA (5 and 20 μM) (FIG. 5A). The percent β-cell proliferation over control was measured by flow cytometry (n=3 wells/condition; #: p<0.05 versus control with no PAHSA treatment; *: p<0.05 versus IL-1β with no PAHSA treatment and control with no PAHSA treatment). MIN6 cells were treated with Cytomix (TNFα+IL-1β+IFN-γ; 5+5+10 ng/mL) in the continuous presence or absence of 5-PAHSA (20 μM) or 9-PAHSA (20 μM) for 24 hours (FIG. 5B) and 48 hours (FIG. 5C). β-cell proliferation was measured by BrdU incorporation into cells (n=10 wells/condition; #: p<0.05 versus control with no PAHSA treatment; *: p<0.05 versus Cytomix with no PAHSA treatment and control with no PAHSA treatment; @: p<0.05 versus Cytomix+9-PAHSA treatment; data are means±SEM).

Figures 6A, 6B, 6C:
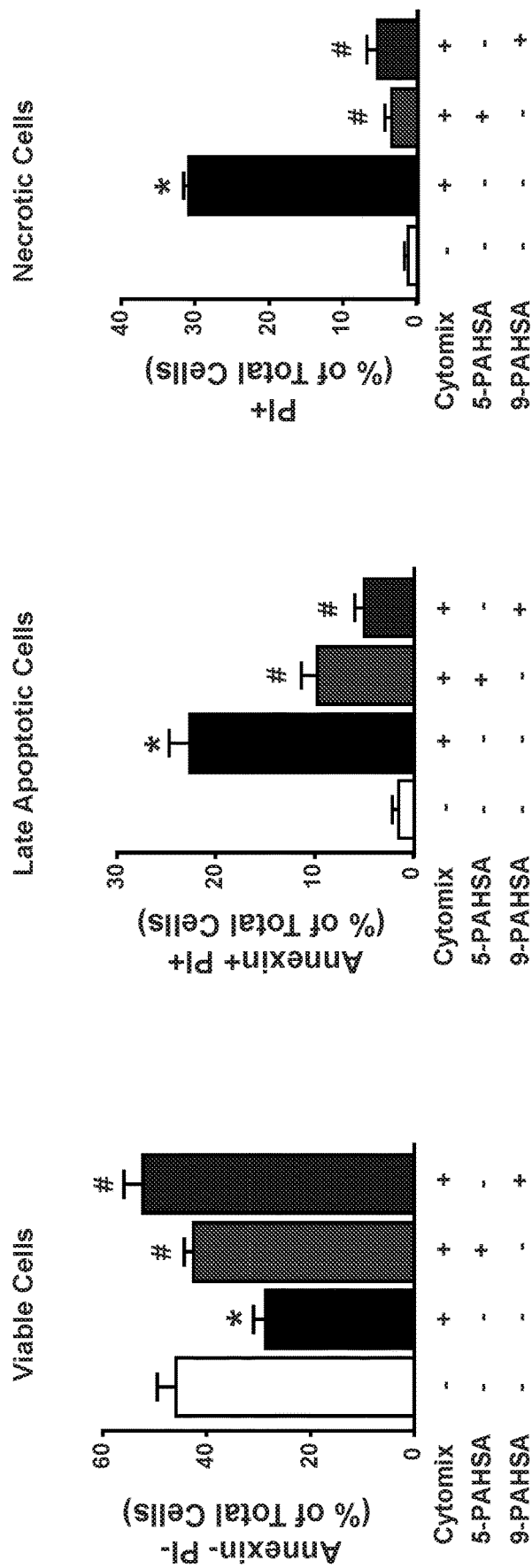

FIGS. 6A-6C show that PAHSAs attenuate cytokine-induced apoptotic and necrotic β-cells in vitro. MIN6 cells were treated with Cytomix (TNFα+IL-1β+IFN-γ; 5+5+10 ng/mL) in the continuous presence or absence of 5-PAHSA (20 μM) or 9-PAHSA (20 μM) for 24 hours and stained with Annexin V and propidium iodide (PI) to evaluate the number of viable cells (FIG. 6A), late apoptotic cells (FIG. 6B) and necrotic cells (FIG. 6C) (n=6 wells/condition; *: p<0.05 versus control with no PAHSA treatment; #: p<0.05 versus Cytomix with no PAHSA treatment; data are means±SEM).

Figure 7A:
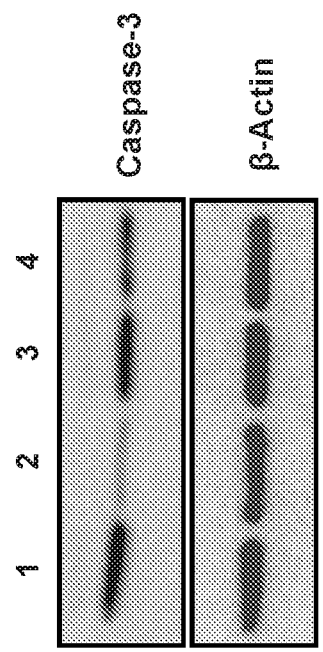
Figure 7B:
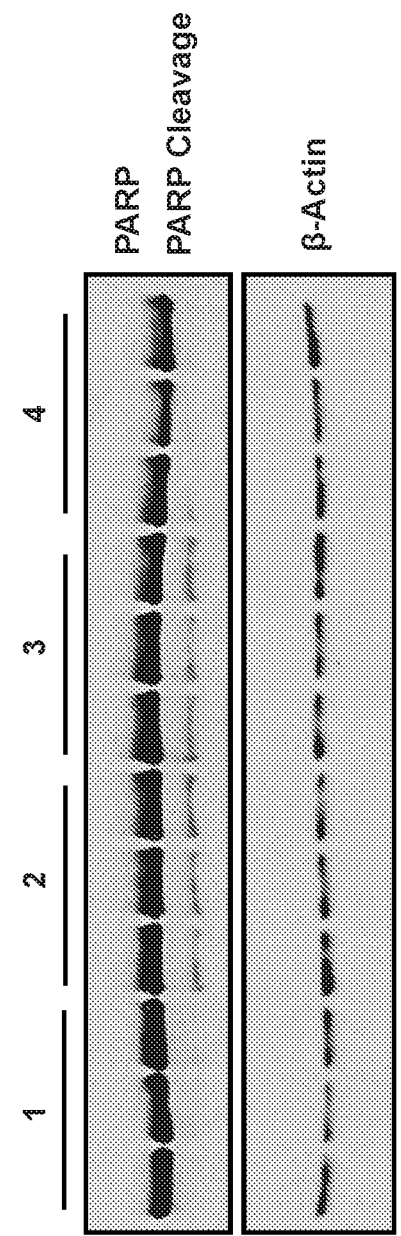

FIGS. 7A and 7B show that PAHSAs attenuate pancreatic β-cell death in vitro by inhibiting caspase-3 degradation and endoplasmic reticulum stress. MIN6 cells were treated with either Cytomix (TNFα+IL-1β+IFN-γ; 5+5+10 ng/mL) for 24 hours (FIG. 7A) or thapsigargin (2 μmol/L) for 6 hours (FIG. 7B) in the continuous presence or absence of 5-PAHSA (20 μM) or 9-PAHSA (20 μM). Western blot analysis was performed with the cell lysates for caspase-3 and PARP cleavage (n=4-6 wells/condition). 1: control; 2: Cytomix; 3: Cytomix+5-PAHSA; 4: Cytomix+9-PAHSA (FIG. 7A). 1: control; 2: thapsigargin; 3: thapsigargin+9-PAHSA; 4: thapsigargin+5-PAHSA (FIG. 7B).

Figure 8:
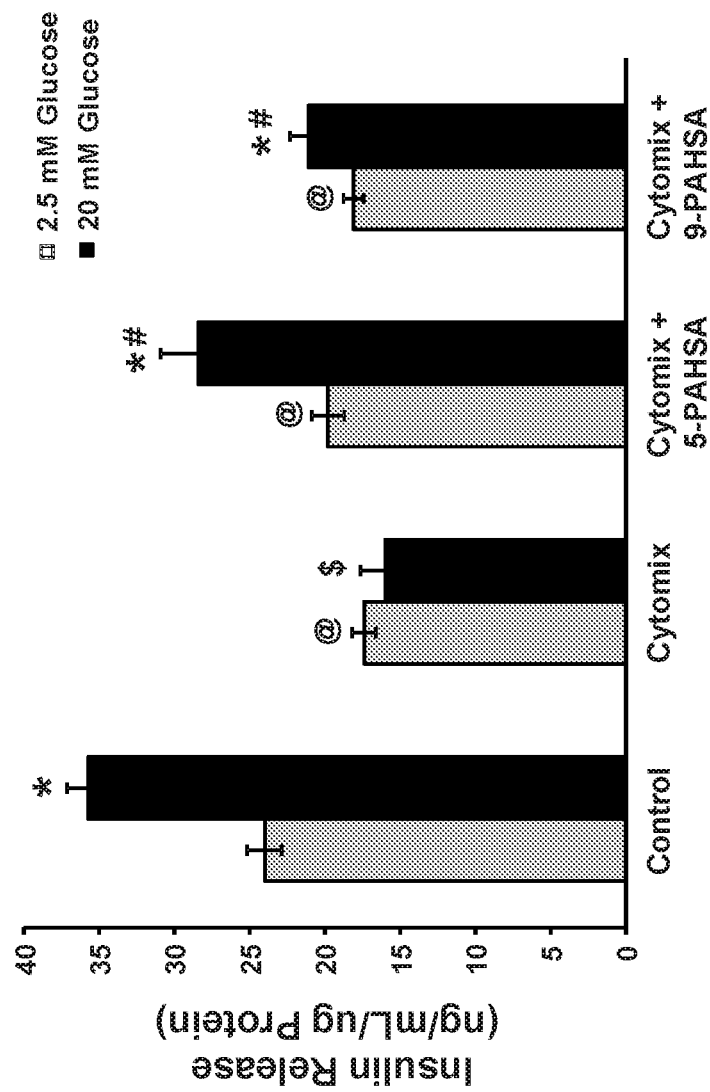

FIG. 8 shows that PAHSAs attenuate cytokine-mediated decrease in glucose stimulated insulin secretion in vitro. MIN6 cells were treated with Cytomix (TNFα+IL-1β+IFN-γ; 5+5+10 ng/mL) in the continuous presence or absence of 5-PAHSA (20 μM) or 9-PAHSA (20 μM) for 24 hours. At the end of incubation, cells were stimulated with low (2.5 mM) or high (20 mM) glucose for 45 minutes in the presence or absence of PAHSAs and insulin released in the buffer was analyzed by ELISA (n=10 wells/condition; @: p<0.05 versus control 2.5 mM glucose; *: p<0.05 versus respective 2.5 mM glucose; $: p<0.05 versus control 20 mM glucose; #: p<0.05 versus 20 mM glucose control and 20 mM glucose and Cytomix; data are means±SEM).

Figure 9A:
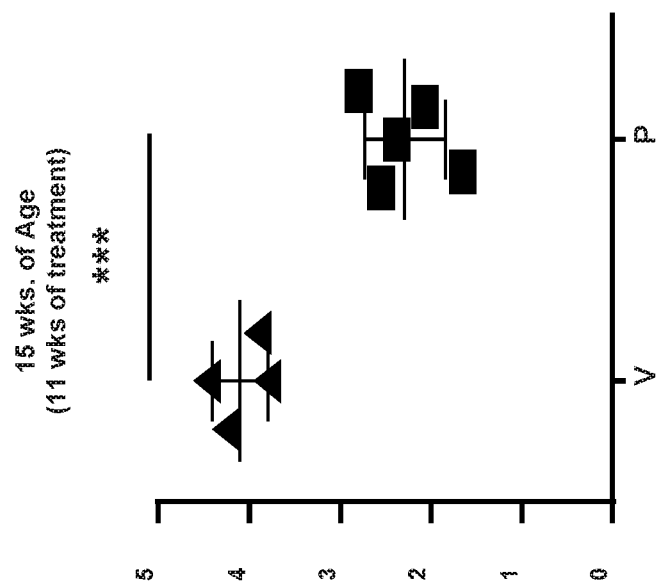
Figure 9A:
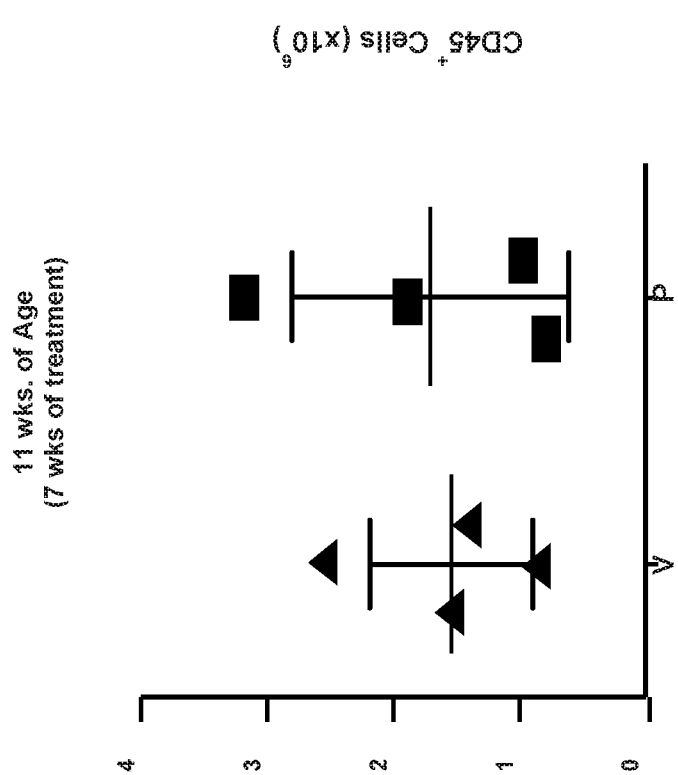

FIGS. 9A-9E show that chronic 5- and 9-PAHSA treatment reduces pancreatic T-cell activation in NOD mice. Total number of CD45+ cells in pancreata from mice treated with 5- and 9-PAHSA or vehicle for 7 weeks (11 weeks of age; left panel) or 11 weeks (15 weeks of age; right panel) (n=4-5/group; *p<0.05 versus vehicle-treated mice) (FIG. 9A). Proportions of CD69$^+$ T (FIG. 9B) and IFNγ$^+$ (FIG. 9C) cells in the CD4 and CD8 population in the pancreas of 5- and 9-PAHSA- or vehicle-treated mice. Left, representative cytofluorometric dot plots; right, summary data. n=4-5. *p<0.05 versus vehicle-treated mice. Proportions of Foxp3$^+$ cells within the CD4 T-cell population in the pancreas of 5- and 9-PAHSA- or vehicle-treated mice (left: representative cytofluorometric dot plots; right: summary data; n=4-5) (FIG. 9D). Foxp3$^+$ mean fluorescence intensity in the pancreas of 5- and 9-PAHSA- or vehicle-treated mice (n=4-5; *p<0.05 versus vehicle-treated mice) (FIG. 9E). Data are means±SEM. V=vehicle; P=5- and 9-PAHSA.

Figure 10A:
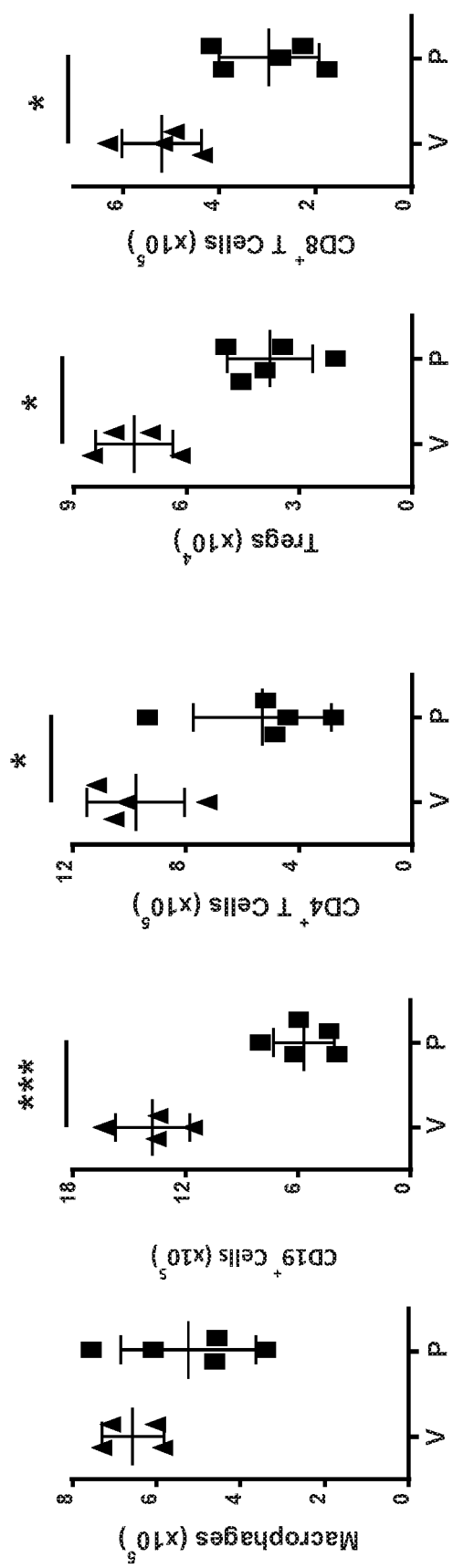

FIG. 10A shows summary data on the total number of major immune cell subsets from the pancreas of 5- and 9-PAHSA- or vehicle-treated mice. n=4-5. *p<0.05 vs. vehicle treated mice. Data are means±SEM. V=vehicle; P=5- and 9-PAHSA.

Figure 10B:
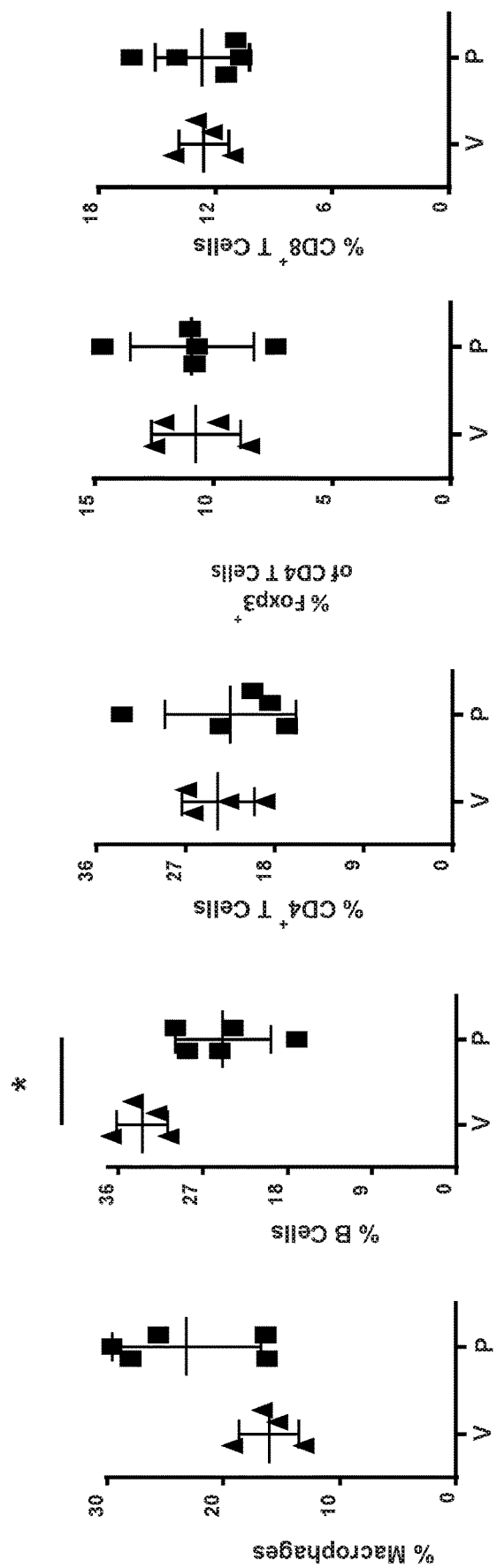

FIG. 10B shows summary data on major immune-cell subsets as a fraction of CD45+ cells from the pancreas of 5- and 9-PAHSA- or vehicle-treated mice. n=4-5. *p<0.05 vs. vehicle treated mice. Data are means±SEM. V=vehicle; P=5- and 9-PAHSA.

Figure 10C:
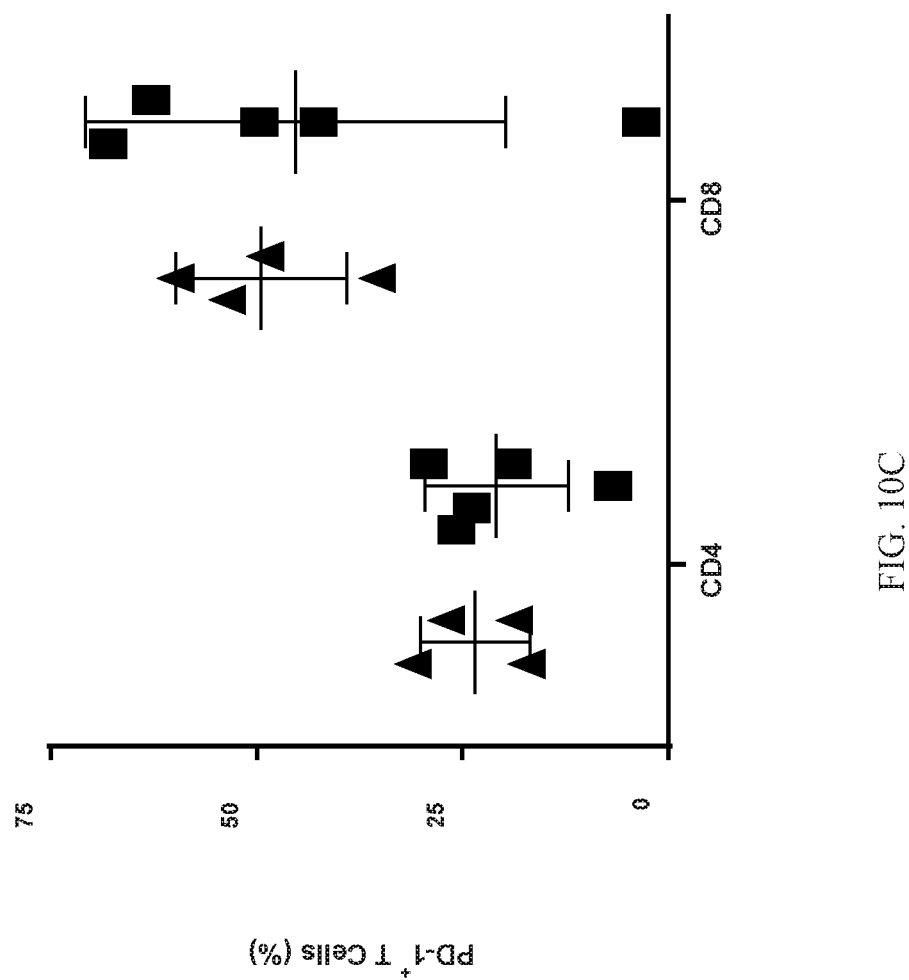

FIG. 10C shows the proportions of PD-1+ T cells within the CD4 and CD8 cell populations in the pancreas of 5- and 9-PAHSA- or vehicle-treated mice. n=4-5. Data are means±SEM. V=vehicle; P=5- and 9-PAHSA.

FIGS. 11A-11D show that PAHSA treatment increases islet β-cell proliferation under cytokine stress in vivo. Female NOD mice were treated with vehicle or 5- and 9-PAHSA for 7 weeks starting at 4 weeks of age to measure islet inflammation and architecture (FIG. 11A), percent β-cell and α-cell area per islet (FIG. 11B), β-cell proliferation (FIG. 11C) and liver proliferation (FIG. 11D). n=5-7/group. *p<0.05 versus vehicle-treated mice.

Figure 12:
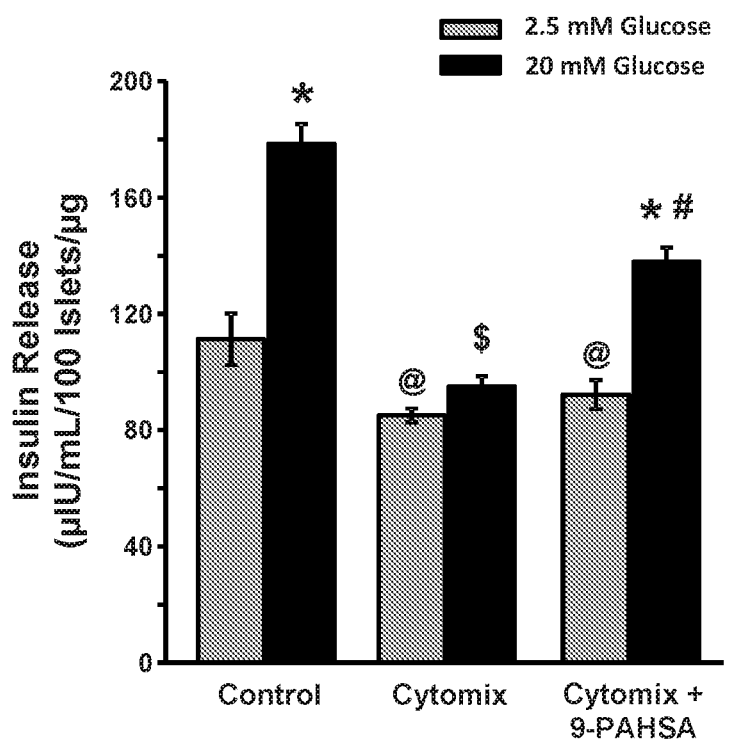

FIG. 12 shows that PAHSAs augment glucose-stimulated insulin secretion during cytokine-induced β-cell distress. Human islets were treated with Cytomix (TNFα+IL-1β+IFN-γ; 5+5+10 ng/mL) in the continuous presence or absence of 9-PAHSA (20 μM) for 24 hours. At the end of incubation, cells were stimulated with low (2.5 mM) or high (20 mM) glucose for 45 minutes in the presence or absence of 9-PAHSA, and insulin released in the buffer was analyzed by ELISA. n=4 wells/condition. @ p<0.05 versus control 2.5 mM glucose; *p<0.05 versus respective 2.5 mM glucose; $ p<0.05 versus control 20 mM glucose; #p<0.05 versus control and Cytomix 20 mM glucose. Data are means±SEM.

DETAILED DESCRIPTION OF THE INVENTION

A description of example embodiments of the invention follows.

Provided herein is a method for treating type 1 diabetes in a subject in need thereof, comprising administering to the subject a therapeutically effective amount of a fatty acid ester of a hydroxy fatty acid (FAHFA), or a pharmaceutically acceptable salt thereof.

As used herein, the singular forms "a", "an" and "the" include plural referents unless the context clearly dictates otherwise. Thus, for example, reference to "a FAHFA" can include a plurality of FAHFAs. Further, the plurality can comprise more than one of the same FAHFA or a plurality of different FAHFAs.

As used herein, the term "treat," "treating" or "treatment" is defined as the application or administration of a FAHFA, alone or in combination (e.g., with a second FAHFA), to a subject, e.g., a patient, or application or administration of a FAHFA to an isolated tissue or cell, e.g., cell line, from a subject, e.g., a patient, who has a disorder (e.g., a disorder as described herein, such as type 1 diabetes or one or more sequelae of type 1 diabetes), a symptom of a disorder, or a predisposition toward a disorder, in order to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

"Type 1 diabetes" refers to a form of diabetes mellitus in which the immune system destroys insulin-producing beta cells in the pancreas, resulting in a lack of insulin. Type 1 diabetes can be associated with β-cell apoptosis or necrosis and can lead to blindness, kidney failure, neuropathy, cardiovascular disease, limb amputation resulting from infection, diabetic ketoacidosis, coma, dehydration, hypoglycemia (e.g., from insulin treatment), mycotic infection and sexual dysfunction.

As used herein, the term "subject" is intended to include human and non-human animals. Example human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, cow, pig, etc., and companion animals (dog, cat, horse, etc.). In some embodiments, the subject is a human.

As used herein, an amount of a compound effective to treat a disorder, or a "therapeutically effective amount," refers to an amount of the compound which is effective, upon single or multiple dose administration to a subject or a cell, in curing, alleviating, relieving or improving one or more symptoms of a disorder.

As used herein, an amount of a compound effective to prevent a disorder, or a "prophylactically effective amount," refers to an amount effective, upon single- or multiple-dose administration to a subject, in preventing or delaying the onset or recurrence of a disorder or one or more symptoms of the disorder.

"Fatty acid ester of a hydroxy fatty acid" or "FAHFA" refers to an estolide having an estolide number of 1, in which a hydroxy fatty acid is esterified at its hydroxy group by another fatty acid. In the present invention, the hydroxy group of the fatty acid is not on the terminal carbon of the fatty acid. A FAHFA is a free acid, but may also be in the form of a salt (e.g., a pharmaceutically acceptable salt) or may be incorporated into other structures, including, but not limited to, phospholipids, glycerophospholipids, carbohydrates, polypeptides, proteins (e.g., analogous to cysteine palmitoylation and myristoylation), di- and triglycerides, or conjugated to other molecules involved in metabolism, particularly lipid metabolism, such as coenzyme A (CoA) or acyl carnitine. FAHFAs are described in International Publication No. WO 2014/144777 and International Publication No. WO 2013/166431. When a FAHFA is incorporated into another structure or conjugated to another molecule involved in metabolism, the FAHFA can be derivatized at one or more positions including the carboxylic acid of the hydroxy fatty acid or the aliphatic group of the hydroxy fatty acid or the fatty acid ester by, for example, an O-containing, N-containing or S-containing species or linkage or a hydrocarbon species or linkage.

In some embodiments of the methods disclosed herein, the FAHFA, or a pharmaceutically acceptable salt thereof, is incorporated into another structure (e.g., a phospholipid, glycerophospholipid, carbohydrate, polypeptide, protein, di- or triglyceride) or conjugated to another molecule (e.g., CoA, acyl carnitine) involved in metabolism (e.g., lipid metabolism).

"Hydroxy" refers to —OH.

In certain embodiments of the invention, the hydroxy fatty acid of the FAHFA is hydroxytetradecanoic acid (14 carbon atoms), hydroxypentadecanoic acid (15 carbon atoms), hydroxypalmitic acid (16 carbon atoms), hydroxyheptadecanoic acid (17 carbon atoms), hydroxystearic acid (18 carbon atoms), hydroxynonadecylic acid (19 carbon atoms), hydroxyicosanoic acid (20 carbon atoms), hydroxyhenicosanoic acid (21 carbon atoms), hydroxydocosanoic acid (22 carbon atoms), hydroxytricosanoic acid (23 carbon atoms) or hydroxytetracosanoic acid (24 carbon atoms), where, for each of the above, the hydroxy group may substitute any of positions 2 through p-1, where p is the total number of carbons in the fatty acid.

The aliphatic chain of the fatty acid ester can be saturated or unsaturated, linear or branched and can have, for example, from 1 to 25, from 1 to 20, from 15 to 20 or 15, 16 or 17 carbon atoms not including the carbonyl carbon atom. Typically, the aliphatic chain of the fatty acid ester is an alkyl.

In some embodiments of the methods provided herein, the FAHFA is represented by structural formula (I):

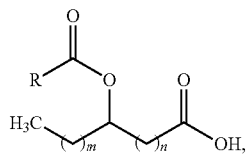

or a pharmaceutically acceptable salt thereof, wherein:
R is an aliphatic group;
m is an integer from 0 to 21;
n is an integer from 0 to 21; and
the sum of m and n is an integer from 11 to 21.

"Aliphatic" means a saturated or unsaturated, branched or straight-chain monovalent hydrocarbon radical having the specified number of carbon atoms. For example, "$C_1$-$C_{20}$ aliphatic group" means an aliphatic group having from one to twenty carbon atoms in a linear or branched arrangement. "Aliphatic" includes stearyl, palmitoyl, myristyl, lauryl, palmitoleyl, oleyl, linoleyl and linolenyl.

In some embodiments, R is a $C_1$-$C_{25}$ aliphatic group. In some embodiments, R is a $C_1$-$C_{20}$ aliphatic group, a $C_{15}$-$C_{20}$ aliphatic group or a $C_{15}$, $C_{16}$ or $C_{17}$ aliphatic group.

In some embodiments, R is an alkyl group. For example, R is a $C_1$-$C_{25}$ alkyl group, a $C_1$-$C_{20}$ alkyl group, a $C_{15}$-$C_{20}$ alkyl group or a $C_{15}$, $C_{16}$ or $C_{17}$ alkyl group.

"Alkyl" means an optionally substituted saturated aliphatic branched or straight-chain monovalent hydrocarbon radical having the specified number of carbon atoms. Thus, "($C_1$-$C_{20}$) alkyl" means an alkyl radical having from one to twenty carbon atoms in a linear or branched arrangement. "Alkyl" includes stearyl, palmitoyl, myristyl and lauryl.

In some embodiments of the methods provided herein, the FAHFA is a palmitoleic acid ester of hydroxy palmitoleic acid (POHPO), a palmitic acid ester of hydroxy palmitoleic acid (PAHPO), an oleic acid ester of hydroxy palmitoleic acid (OAHPO), a stearic acid ester of hydroxy palmitoleic acid (SAHPO), a palmitoleic acid ester of hydroxy palmitic acid (POHPA), a palmitic acid ester of hydroxy palmitic acid (PAHPA), an oleic acid ester of hydroxy palmitic acid (OAHPA), a stearic acid ester of hydroxy palmitic acid (SAHPA), a palmitoleic acid ester of hydroxy oleic acid (POHOA), a palmitic acid ester of hydroxy oleic acid (PAHOA), an oleic acid ester of hydroxy oleic acid (OAHOA), a stearic acid ester of hydroxy oleic acid (SAHOA), a palmitoleic acid ester of hydroxy stearic acid (POHSA), a palmitic acid ester of hydroxy stearic acid (PAHSA), an oleic acid ester of hydroxy stearic acid (OAHSA) or a stearic acid ester of hydroxy stearic acid (PAHSA), or a stereoisomer of any of the foregoing, or a combination of any of the foregoing. In a particular embodiment, the FAHFA is a PAHSA, or a pharmaceutically acceptable salt thereof, for example, O-palmitoyl-5-hydroxystearic acid (5-PAHSA), O-palmitoyl-7-hydroxystearic acid (7-PAHSA), O-palmitoyl-8-hydroxystearic acid (8-PAHSA), O-palmitoyl-9-hydroxystearic acid (9-PAHSA), O-palmitoyl-10-hydroxystearic acid (10-PAHSA), O-palmitoyl-11-hydroxystearic acid (11-PAHSA) or O-palmitoyl-12/13-hydroxystearic acid (12/13-PAHSA), a pharmaceutically acceptable salt of any of the foregoing or a combination of any of the foregoing.

In a more particular embodiment, the PAHSA is O-palmitoyl-5-hydroxystearic acid (5-PAHSA) or O-palmitoyl-9-hydroxystearic acid (9-PAHSA), or a pharmaceutically acceptable salt of any of the foregoing or a combination of any of the foregoing.

In some embodiments of the methods described herein, the FAHFA, or its pharmaceutically acceptable salt, is administered in combination with a second FAHFA, or a pharmaceutically acceptable salt thereof. For example, in some embodiments, 5-PAHSA, or a pharmaceutically acceptable salt thereof, is administered in combination with 9-PAHSA, or a pharmaceutically acceptable salt thereof.

In some embodiments, when the FAHFA (e.g., 5-PAHSA), or a pharmaceutically acceptable salt thereof, is administered in combination with a second FAHFA (e.g., 9-PAHSA), or a pharmaceutically acceptable salt thereof, the FAHFA and the second FAHFA can be administered in a ratio (e.g., a molar ratio) of about 1:3, about 1:2, about 1:1, about 2:1 or about 3:1. In some embodiments, when the FAHFA (e.g., 5-PAHSA), or a pharmaceutically acceptable salt thereof, is administered in combination with a second FAHFA (e.g., 9-PAHSA), or a pharmaceutically acceptable salt thereof, the FAHFA and the second FAHFA can be administered in a ratio (e.g., a molar ratio) of about 1:1. In some embodiments, when the FAHFA (e.g., 5-PAHSA), or a pharmaceutically acceptable salt thereof, is administered in combination with a second FAHFA (e.g., 9-PAHSA), or a pharmaceutically acceptable salt thereof, the FAHFA and the second FAHFA can be administered in a ratio (e.g., a molar ratio) of about 2:1.

O-palmitoyl-12/13-hydroxystearic acid (12/13-PAHSA) refers to a mixture of O-palmitoyl-12-hydroxystearic acid (12-PAHSA) and O-palmitoyl-13-hydroxystearic acid (13-PAHSA).

As used herein, palmitoleic acid ester of hydroxy palmitoleic acid (POHPO) is a FAHFA in which hydroxy palmitoleic acid is esterified at its hydroxy group by palmitoleic acid.

As used herein, palmitic acid ester of hydroxy palmitoleic acid (PAHPO) is a FAHFA in which hydroxy palmitoleic acid is esterified at its hydroxy group by palmitic acid.

As used herein, oleic acid ester of hydroxy palmitoleic acid (OAHPO) is a FAHFA in which hydroxy palmitoleic acid is esterified at its hydroxy group by oleic acid.

As used herein, stearic acid ester of hydroxy palmitoleic acid (SAHPO) is a FAHFA in which hydroxy palmitoleic acid is esterified at its hydroxy group by stearic acid.

As used herein, palmitoleic acid ester of hydroxy palmitic acid (POHPA) is a FAHFA in which hydroxy palmitic acid is esterified at its hydroxy group by palmitoleic acid.

As used herein, palmitic acid ester of hydroxy palmitic acid (PAHPA) is a FAHFA in which hydroxy palmitic acid is esterified at its hydroxy group by palmitic acid.

As used herein, oleic acid ester of hydroxy palmitic acid (OAHPA) is a FAHFA in which hydroxy palmitic acid is esterified at its hydroxy group by oleic acid.

As used herein, stearic acid ester of hydroxy palmitic acid (SAHPA) is a FAHFA in which hydroxy palmitic acid is esterified at its hydroxy group by stearic acid.

As used herein, palmitoleic acid ester of hydroxy oleic acid (POHOA) is a FAHFA in which hydroxy oleic acid is esterified at its hydroxy group by palmitoleic acid.

As used herein, palmitic acid ester of hydroxy oleic acid (PAHOA) is a FAHFA in which hydroxy oleic acid is esterified at its hydroxy group by palmitic acid.

As used herein, oleic acid ester of hydroxy oleic acid (OAHOA) is a FAHFA in which hydroxy oleic acid is esterified at its hydroxy group by oleic acid.

As used herein, stearic acid ester of hydroxy oleic acid (SAHOA) is a FAHFA in which hydroxy oleic acid is esterified at its hydroxy group by stearic acid.

As used herein, palmitoleic acid ester of hydroxy stearic acid (POHSA) is a FAHFA in which hydroxy stearic acid is esterified at its hydroxy group by palmitoleic acid.

As used herein, palmitic acid ester of hydroxy stearic acid (PAHSA) is a FAHFA in which hydroxy stearic acid is esterified at its hydroxy group by palmitic acid.

As used herein, oleic acid ester of hydroxy stearic acid (OAHSA) is a FAHFA in which hydroxy stearic acid is esterified at its hydroxy group by oleic acid.

As used herein, stearic acid ester of hydroxy stearic acid (SAHSA) is a FAHFA in which hydroxy stearic acid is esterified at its hydroxy group by stearic acid.

In some embodiments of the methods provided herein (e.g., the methods for treating type 1 diabetes, the methods for treating one or more sequelae of type 1 diabetes, the methods for inhibiting cytokine-induced apoptosis or necrosis of a β-cell, promoting islet viability of a β-cell or stimulating proliferation of a β-cell, etc.), a compound represented by structural formula (II):

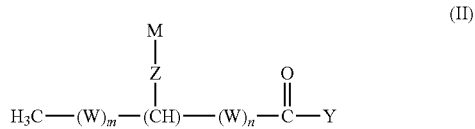

(II)

or a salt (e.g., pharmaceutically acceptable salt) thereof, is administered to a subject or contacted with a cell. In the compound of structural formula (II):

m is an integer from 0 to 21;
n is an integer from 0 to 21;
the sum of m and n is an integer from 11 to 21;
W, for each occurrence, is independently (CR$^1$R$^2$) or (C(R$^3$)=C(R$^4$));
Z is —NH(CO)—, —O—, —O(CO)—, —S—, —NH—, —NO—, —O(CO)O—, —O(CO)NH—, —NH(CO)O—, —SO$_2$—, —OP(O)(OR$^{12}$)O—, —Se—, —SeO—, —N(R$^{13}$)— or —O(CO)N(R$^{13}$)—;
Y is H, OH, OR$^5$, NHR$^6$, N(R$^7$)$_2$, SR$^8$, or halo;
R$^1$, R$^2$, R$^3$ and R$^4$, for each occurrence, are independently selected from H, (C$_6$-C$_{12}$)aryl, (C$_5$-C$_{12}$)heteroaryl, —(CO)(C$_1$-C$_6$)alkyl, (C$_1$-C$_{12}$)alkyl, (C$_1$-C$_{12}$)alkoxy or hydroxy;
M is selected from (CR$^9$R$^{10}$)$_{11-23}$CH$_3$, (C$_6$-C$_{12}$)aryl, (C$_5$-C$_{12}$)heteroaryl or (C$_{12}$-C$_{24}$)alkenyl, wherein each (C$_6$-C$_{12}$)aryl, (C$_5$-C$_{12}$)heteroaryl and (C$_{12}$-C$_{24}$)alkenyl is optionally and independently substituted at any one or more substitutable positions by (C$_1$-C$_{12}$)alkyl, (C$_1$-C$_{12}$)alkoxy, hydroxy, —NH$_2$, —N((C$_1$-C$_{12}$)alkyl)$_2$, or —S—(C$_1$-C$_{12}$)alkyl;
R$^5$, R$^6$, R$^7$, and R$^8$ are each (C$_1$-C$_{12}$)alkyl, (C$_6$-C$_{12}$)aryl, (C$_5$-C$_{12}$)heteroaryl or (C$_{12}$-C$_{24}$)alkenyl;
R$^9$ and R$^{10}$, for each occurrence, are independently H, (C$_1$-C$_{12}$)alkyl, (C$_1$-C$_{12}$)alkoxy, hydroxy, —NH$_2$, —N[(C$_1$-C$_{12}$)alkyl]$_2$ or —S(C$_1$-C$_{12}$)alkyl;
R$^{12}$ is H, (CR$^9$R$^{10}$)$_{0-23}$CH$_3$, (C$_6$-C$_{12}$)aryl, (C$_5$-C$_{12}$)heteroaryl or (C$_2$-C$_{12}$)alkenyl, wherein each (C$_6$-C$_{12}$)aryl, (C$_5$-C$_{12}$)heteroaryl and (C$_2$-C$_{12}$)alkenyl is optionally and independently substituted at any one or more substitutable positions by (C$_1$-C$_{12}$)alkyl, (C$_1$-C$_{12}$)alkoxy, hydroxy, —NH$_2$, —N((C$_1$-C$_{12}$)alkyl)$_2$ or —S—(C$_1$-C$_{12}$)alkyl; and
R$^{13}$ is (C$_1$-C$_{12}$)alkyl, (C$_6$-C$_{12}$)aryl, (C$_5$-C$_{12}$)heteroaryl, (C$_3$-C$_6$)cycloalkyl or (C$_2$-C$_{12}$)alkenyl.

In certain embodiments of a compound of structural formula (II), when any one of R$^1$ or R$^2$ is hydroxy or (C$_1$-C$_{12}$)alkoxy, then not all R$^9$ and R$^{10}$ are H; when any one of R$^9$ or R$^{10}$ is hydroxy or (C$_1$-C$_{12}$)alkoxy, then not all R$^1$ and are H; and (C$_{12}$-C$_{24}$)alkenyl is not (C$_{17}$)alkenyl or (C$_{19}$)alkenyl.

In particular embodiments, R$^1$ and R$^2$ of structural formula (II), for each occurrence, are independently selected from H, (C$_6$-C$_{12}$)aryl, or (C$_1$-C$_{12}$)alkyl; Z is —NH(CO)—, —O—, —O(CO)—, —O(CO)O—, —O(CO)NH—, or —NH(CO)O—; Y is OH or OR$^5$; and M is (CH$_2$)$_{11-23}$CH$_3$.

In certain embodiments, a FAHFA is detectably labeled. For example, the FAHFA can be isotopically labeled and/or ester- or amide-bound to a detectable moiety, such as biotin, streptavidin, GST, a fluorous affinity tag, an alkyne suitable for click chemistry, an epitope tag such as FLAG, 6×His, or another affinity tag. In certain embodiments, the invention also provides a FAHFA derivative incorporated into structures such as phospholipids, glycerophospholipids, carbohydrates, polypeptides and proteins, di- and triglyderides, and conjugates to metabolic cofactors such as CoA or acyl carnitine. In further aspects, the invention provides compositions and formulations comprising any of the foregoing.

Unless otherwise stated, structures depicted herein are also meant to include all isomeric (e.g., enantiomeric, diastereomeric, geometric and conformational) forms of the structure; for example, the R and S configurations for each asymmetric center, Z and E double bond isomers, rotamers. Therefore, single stereochemical isomers as well as enantiomeric, diastereomeric, geometric and conformational mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds produced by the replacement of a hydrogen with deuterium or tritium, or of a carbon with a $^{13}$C- or $^{14}$C-enriched carbon are within the scope of this invention. Such compounds are useful, for example, as analytical tools, as probes in biological assays, or as therapeutic agents in accordance with the present invention.

The term "stereoisomer" is a general term for all isomers of an individual molecule that differ only in the orientation of their atoms in space. It includes mirror image isomers (enantiomers), geometric (cis/trans) isomers, conformational isomers (e.g., rotamers) and isomers of compounds with more than one chiral center that are not mirror images of one another (diastereomers). For example, Structural Formula (I):

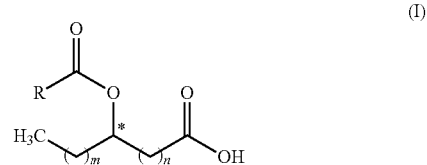

(I)

is meant to denote both

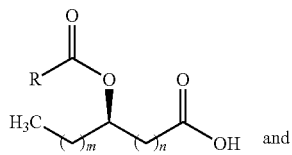 (Ia)

and

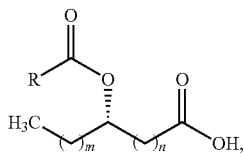 (Ib)

and mixtures thereof. Structural Formula (II):

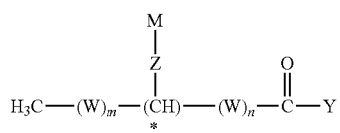 (II)

is meant to denote both

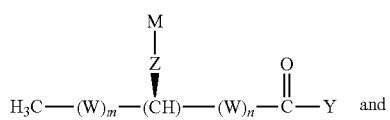 (IIa)

and

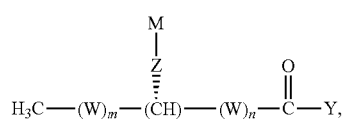 (IIb)

and mixtures thereof. In some embodiments, greater than about 85% of compound molecules in a mixture of the compound of Structural Formula (Ia), (Ib), (IIa) or (IIb) possess the indicated stereochemistry. In some embodiments, greater than about 90%, greater than about 95%, greater than about 98%, greater than about 99%, greater than about 99.5% or greater than about 99.8% of compound molecules in a mixture of the compound possess the indicated stereochemistry.

The term "conformational isomer" is a term for all isomers of an individual molecule that can be interconverted exclusively by rotation around a single bond.

In certain embodiments, the FAHFA is a (D)-isomer. In some embodiments, greater than about 85% of the FAHFA molecules in a mixture of the FAHFA are (D)-isomers of the FAHFA. In some embodiments, greater than about 90%, greater than about 95%, greater than about 98%, greater than about 99%, greater than about 99.5% or greater than about 99.8% of the FAHFA molecules in a mixture of the FAHFA are (D)-isomers of the FAHFA.

In alternative embodiments, the FAHFA is an (L)-isomer. In some embodiments, greater than about 85% of the FAHFA molecules in a mixture of the FAHFA are (L)-isomers of the FAHFA. In some embodiments, greater than about 90%, greater than about 95%, greater than about 98%, greater than about 99%, greater than about 99.5% or greater than about 99.8% of the FAHFA molecules in a mixture of the FAHFA are (L)-isomers of the FAHFA.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19. Pharmaceutically acceptable salts of the compounds described herein include salts derived from suitable inorganic and organic bases that are compatible with the treatment of patients. Typically, pharmaceutically acceptable salts should be "generally regarded as safe" (GRAS), e.g., are physiologically tolerable and do not typically produce an allergic or similar untoward reaction, such as gastric upset, dizziness and the like, when administered to an animal, such as a human. Preferably, as used herein, the term "pharmaceutically acceptable" means approved by a regulatory agency of the federal government or a state government or listed in the U.S. Pharmacopeia or other generally recognized pharmacopeia for use in animals.

Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations (e.g., $N^+(C_{1-4}alkyl)_4$) formed using counterions such as halide, hydroxide, carboxyl, sulfate, phosphate, nitrate, lower alkyl sulfonate and aryl sulfonate. Illustrative inorganic bases which form suitable salts include, but are not limited thereto, lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection criteria for the appropriate salt will be known to one skilled in the art.

The FAHFAs described herein and their pharmaceutically acceptable salts can be incorporated into pharmaceutical compositions for administration to a subject. In some embodiments, the pharmaceutical composition comprises a therapeutically or prophylactically (e.g., therapeutically) effective amount of a FAHFA, or a pharmaceutically acceptable salt thereof, and a pharmaceutically acceptable carrier, adjuvant, or vehicle. In some embodiments, a pharmaceutical composition is formulated for oral, intravenous, subcutaneous, intraperitoneal or dermatological administration to a subject in need thereof.

The phrase "pharmaceutically acceptable carrier, adjuvant, or vehicle" refers to a non-toxic carrier, adjuvant, or vehicle that does not destroy the pharmacological activity of the compound with which it is formulated and is nontoxic when administered in doses sufficient to deliver a therapeutic amount of a compound. The pharmaceutical compositions disclosed herein can be prepared and administered in accordance with standard procedures (see, e.g., Remington's Pharmaceutical Sciences, Mack Publishing Company, Easton, Pa., and Goodman and Gilman's The Pharmaceutical Basis of Therapeutics, McGraw-Hill, New York, N.Y., the relevant contents of which are incorporated herein by reference, for a general description of the methods for administering various agents for human therapy).

Pharmaceutically acceptable carriers can be solid or liquid. Solid form preparations include powders, tablets, pills, capsules, cachets, suppositories, and dispersible granules. For example, the FAHFAs of the present invention can be in powder form for reconstitution at the time of delivery. A solid carrier can be one or more substances which can also act as diluent, flavoring agent, solubilizer, lubricant, suspending agent, binder, preservative, tablet disintegrating agent, or an encapsulating material. In powders, the carrier can be a finely divided solid which is in a mixture with the finely divided active ingredient. Such pharmaceutical carriers can be sterile liquids, oils, including those of petroleum, animal, vegetable or synthetic origin, such as peanut oil, soybean oil, mineral oil, sesame oil and the like. Carriers such as micelles or dextrans can be used to deliver the agent in an aqueous solution or suspension. Suitable pharmaceutical carriers are described in "Remington's Pharmaceutical Sciences" by E. W. Martin. In some embodiments, preparations contain from about one to about seventy percent of the active pharmaceutical ingredient. In some embodiments, suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration. Liquid form preparations include solutions, suspensions, retention enemas, and emulsions, for example, water or water propylene glycol solutions. For parenteral injection, liquid preparations can be formulated in solution in aqueous polyethylene glycol solution.

Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Other pharmaceutically acceptable carriers, adjuvants and vehicles that can be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be advantageously used to enhance delivery of compounds described herein.

In some embodiments, a FAHFA or its pharmaceutically acceptable salt or a pharmaceutical composition comprising a FAHFA or its pharmaceutically acceptable salt is administered orally, intravenously, subcutaneously, intraperitoneally or dermatologically. A FAHFA or its pharmaceutically acceptable salt or a pharmaceutical composition comprising a FAHFA or its pharmaceutically acceptable salt can also be administered orally, parenterally (including subcutaneously, intramuscularly, intravenously and intradermally), by inhalation spray, topically, rectally, nasally, buccally, vaginally or via an implanted reservoir. In a particular embodiment, the FAHFA or its pharmaceutically acceptable salt or a pharmaceutical composition comprising a FAHFA or its pharmaceutically acceptable salt is administered orally.

The term "parenteral," as used herein, includes subcutaneous, intracutaneous, intravenous, intramuscular, intraocular, intravitreal, intra-articular, intra-arterial, intra-synovial, intrasternal, intrathecal, intralesional, intrahepatic, intraperitoneal intralesional and intracranial injection or infusion techniques.

Orally acceptable dosage forms include, but are not limited to, capsules, tablets, aqueous suspensions, dispersions and solutions. In the case of tablets for oral use, carriers commonly used include lactose and corn starch. Lubricating agents, such as magnesium stearate, are also typically added. When aqueous suspensions and/or emulsions are required for oral use, the active ingredient can be suspended or dissolved in an oily phase and combined with emulsifying and/or suspending agents. If desired, certain sweetening, flavoring or coloring agents can also be added. An oral formulation can be formulated for immediate release or sustained/delayed release.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders, such as carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium salts, g) wetting agents, such as acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using excipients such as lactose or milk sugar, as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

A FAHFA can also be in micro-encapsulated faun with one or more excipients, as noted above. In such solid dosage forms, the FAHFA can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose.

Pharmaceutical compositions for oral administration may be designed to protect the active ingredient against degradation as it passes through the alimentary tract, for example, by an outer coating on a tablet or capsule.

In another embodiment, a FAHFA can be provided in an extended (or "delayed" or "sustained") release composition. This delayed-release composition comprises a FAHFA or a pharmaceutically acceptable salt thereof in combination with a delayed-release component. Such a composition allows targeted release of a FAHFA into the lower gastrointestinal tract, for example, into the small intestine, the large intestine, the colon and/or the rectum. In certain embodiments, the delayed-release composition comprising a FAHFA further comprises an enteric or pH-dependent coating, such as cellulose acetate phthalates and other phthalates (e.g., polyvinyl acetate phthalate, methacrylates (Eudragits)). Alternatively, the delayed-release composition provides controlled release to the small intestine and/or colon by the provision of pH-sensitive methacrylate coatings, pH-sensitive polymeric microspheres, or polymers that undergo degradation by hydrolysis. The delayed-release composition can be formulated with hydrophobic or gelling excipients or coatings. Colonic delivery can further be provided by coatings that are digested by bacterial enzymes such as amylose or pectin, by pH-dependent polymers, by hydrogel plugs swelling with time (Pulsincap), by time-dependent hydrogel coatings and/or by acrylic acid linked to azoaromatic bonds coatings.

In certain embodiments, the delayed-release composition comprises hypromellose, microcrystalline cellulose, and a lubricant. The mixture of a FAHFA, hypromellose and microcrystalline cellulose can be formulated into a tablet or capsule for oral administration. In certain embodiments, the mixture is granulated and pressed into tablets.

Alternatively, pharmaceutically acceptable compositions of this invention can be administered in the form of suppositories for rectal administration. These can be prepared by mixing a FAHFA with a suitable non-irritating excipient that is solid at room temperature but liquid at rectal temperature and, therefore, will melt in the rectum to release the drug. Such materials include cocoa butter, beeswax and polyethylene glycols.

Pharmaceutically acceptable compositions can also be administered topically, especially when the target of treatment includes areas or organs readily accessible by topical application, including diseases of the eye, the skin, or the lower intestinal tract.

Topical application for the lower intestinal tract can be effected in a rectal suppository formulation (see above) or in a suitable enema formulation. Topically-transdermal patches can also be used.

For other topical applications, pharmaceutically acceptable compositions can be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water and penetration enhancers. Alternatively, pharmaceutically acceptable compositions can be formulated in a suitable lotion or cream containing the active component suspended or dissolved in one or more pharmaceutically acceptable carriers. Alternatively, the pharmaceutical composition can be formulated with a suitable lotion or cream containing a FAHFA suspended or dissolved in a carrier with suitable emulsifying agents. In some embodiments, suitable carriers include, but are not limited to, mineral oil, sorbitan monostearate, polysorbate 60, cetyl esters wax, cetearyl alcohol, 2-octyldodecanol, benzyl alcohol and water. In other embodiments, suitable carriers include, but are not limited to, mineral oil, sorbitan monostearate, polysorbate 60, cetyl esters wax, cetearyl alcohol, 2-octyldodecanol, benzyl alcohol and water and penetration enhancers.

For ophthalmic use, pharmaceutically acceptable compositions can be formulated as micronized suspensions in isotonic, pH-adjusted sterile saline, or, preferably, as solutions in isotonic, pH adjusted sterile saline, either with or without a preservative such as benzylalkonium chloride. Alternatively, for ophthalmic uses, pharmaceutically acceptable compositions can be formulated in an ointment such as petrolatum.

Pharmaceutically acceptable compositions can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

Pharmaceutical compositions can be in the form of a sterile injectable preparation, for example, as a sterile injectable aqueous or oleaginous suspension. This suspension can be formulated according to techniques known in the art using suitable dispersing or wetting agents (such as, for example, Tween 80) or suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

Also, the pharmaceutical composition can contain, if desired, other compatible agents, e.g., pharmaceutical or therapeutic agents. Therapeutic agents include, but are not limited to, peptides, polypeptides, proteins, fusion proteins, nucleic acids and organic molecules. Examples of classes of such agents include, but are not limited to, immunomodulatory agents and agents used to provide relief or to offset the deleterious effects of one or more therapeutic agents (e.g., bisphosphonate to reduce the hypercalcemic effect of glucocorticoids).

One of skill in the art, e.g., a clinician, can determine the suitable dosage and route of administration for one or more FAHFAs or composition of the present invention for administration to an individual, considering the agents chosen, pharmaceutical formulation and route of administration, various patient factors and other considerations. It should be understood that a specific dosage and treatment regimen for any particular subject (e.g., patient) will depend upon a variety of factors, including the activity of the specific compound employed, the age, body weight, general health, sex, diet, time of administration, rate of excretion, drug combination, the judgment of the treating physician and the severity of the particular disease being treated. The amount of a FAHFA to be combined with the carrier materials to produce a pharmaceutical composition in a single dosage form will vary depending upon the host treated, the particular mode of administration and the activity of the compound employed. Preferably, compositions should be formulated so that a dosage of between 0.01-100 mg/kg body weight/day of the FAHFA, or a pharmaceutically acceptable salt thereof, can be administered to a subject receiving the composition. Preferably, the dosage does not cause or produces minimal or no adverse side effects.

In standard multi-dosing regimens, a pharmacological agent may be administered on a dosage schedule that is designed to maintain a pre-determined or optimal plasma concentration in the subject undergoing treatment. A FAHFA, or a pharmaceutically acceptable salt thereof, can be added at any appropriate dosage ranges or therapeutically effective amount, for example, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.5 mg/kg, 2.0 mg/kg, 2.5 mg/kg, 3.0 mg/kg, 4.0 mg/kg, 5.0 mg/kg, 6.0 mg/kg, 7.0 mg/kg, 8.0 mg/kg, 9.0 mg/kg, 10.0 mg/kg, 11.0 mg/kg, 12.0 mg/kg, 13.0 mg/kg, 14.0 mg/kg, 15.0 mg/kg, 16.0 mg/kg, 17.0 mg/kg, 18.0 mg/kg, 19.0 mg/kg, 20.0 mg/kg, 30 mg/kg, 40 mg/kg, 50 mg/kg 60 mg/kg, 70 mg/kg, 80 mg/kg, 90 mg/kg and 100 mg/kg. In one embodiment, the dosage of a FAHFA, or a pharmaceutically acceptable salt thereof, is from about 0.1 mg/kg to about 100 mg/kg or from about 0.1 mg/kg to about 15 mg/kg per administration.

A FAHFA or a pharmaceutically acceptable salt thereof can be administered once, at least once, twice, at least twice, three times, or at least three times per day. A FAHFA or a pharmaceutically acceptable salt thereof can be administered once, at least once, twice, at least twice, three times, at least three times, four times, at least four times, five times, at least five times, six times per week, or at least six times per week. A FAHFA or a pharmaceutically acceptable salt thereof can be administered once per month, at least once per month, twice per month, at least twice per month, three times per month or at least three times per month. A FAHFA or a pharmaceutically acceptable salt thereof can be administered once per year, at least once per year, twice per year, at least twice per year, three times per year, at least three times per year, four times per year, at least four times per year, five times per year, at least five times per year, six times per year or at least six times per year.

A FAHFA or a pharmaceutically acceptable salt thereof can be administered as part of a combination therapy (e.g., with a second FAHFA or a pharmaceutically acceptable salt thereof, and/or with one or more other therapeutic agents). The FAHFA can be administered before, after or concurrently with the second FAHFA and/or one or more other therapeutic agents. In some embodiments, the FAHFA and the second FAHFA and/or other therapeutic agent can be co-administered simultaneously (e.g., concurrently) as either separate formulations or as a joint formulation. Alternatively, the agents can be administered sequentially, as separate compositions, within an appropriate time frame, as determined by the skilled clinician (e.g., a time sufficient to allow an overlap of the pharmaceutical effects of the therapies). A FAHFA and a second FAHFA and/or one or more other therapeutic agents can be administered in a single dose or in multiple doses, in an order and on a schedule suitable to achieve a desired therapeutic effect.

Upon improvement of a subject's condition, a maintenance dose of a compound, composition or combination of this invention can be administered, if necessary. Subsequently, the dosage or frequency of administration, or both, can be reduced, as a function of the symptoms, to a level at which the improved condition is retained when the symptoms have been alleviated to the desired level. Subjects may, however, require intermittent treatment on a long-term basis upon recurrence of disease symptoms.

Also provided herein is a method for treating one or more sequelae of type 1 diabetes in a subject in need thereof, comprising administering to the subject a therapeutically effective amount of a FAHFA, or a pharmaceutically acceptable salt thereof.

"Sequelae of type 1 diabetes" refers to any disorder or condition for which type 1 diabetes is a risk factor or that results from type 1 diabetes. Sequelae of type 1 diabetes include, but are not limited to, blindness, renal disease (e.g., proteinuria, hypertension, renal insufficiency, renal failure), neurologic disease (e.g., peripheral neuropathy such as weakness, pain, numbness, loss of sense of heat and cold; autonomic neuropathy such as digestive problems, orthostatic hypotension, bladder infections, erectile dysfunction, heart problems; stroke), cardiovascular disease (e.g., coronary artery disease, angina, myocardial ischemia, myocardial infarction, peripheral vascular disease), limb amputation resulting from infection, diabetic ketoacidosis, coma, dehydration, hypoglycemia (e.g., from insulin treatment), mycotic infection and sexual dysfunction. In some embodiments of the methods disclosed herein, one or more sequelae includes a cardiovascular disease for which type 1 diabetes is a risk factor, a renal disease for which type 1 diabetes is a risk factor, a neurologic disease for which type 1 diabetes is a risk factor, blindness, limb amputation, diabetic ketoacidosis, coma, dehydration, hypoglycemia, mycotic infection or sexual dysfunction.

Also provided herein is a method for inhibiting cytokine-induced apoptosis or necrosis of a β-cell, promoting islet viability of a β-cell or stimulating proliferation of a β-cell, comprising contacting the β-cell with a FAHFA, or a pharmaceutically acceptable salt thereof.

Also provided herein is a method for treating insulitis in a subject in need thereof, comprising administering to the subject a therapeutically effective amount of a FAHFA, or a pharmaceutically acceptable salt thereof.

Also provided herein is a method for inhibiting caspase-3 degradation or cleavage of poly(ADP-ribose) polymerase (PARP) in a cell, comprising contacting the cell with a FAHFA, or a pharmaceutically acceptable salt thereof.

Also provided herein is a method for inhibiting cell death induced by endoplasmic reticulum stress, comprising contacting a cell with a FAHFA, or a pharmaceutically acceptable salt thereof.

Also provided herein is a method for inhibiting leukocyte infiltration or T-cell activation, comprising administering to a subject a therapeutically or prophylactically (e.g., therapeutically) effective amount of a FAHFA, or a pharmaceutically acceptable salt thereof.

Also provided herein is a method for stimulating insulin secretion (e.g., stimulating glucose-stimulated insulin secretion (GSIS)) in a cell (e.g., a pancreatic beta cell), comprising administering to the cell a FAHFA, or a pharmaceutically acceptable salt thereof.

In any of the aforementioned methods, the cell can be in a subject (e.g., a human subject). Further, in certain embodiments of the aforementioned methods, the cell, particularly when the cell is in a subject (e.g., a subject having a disorder such as type 1 diabetes, one or more sequelae of type 1 diabetes or insulitis), is contacted with a therapeutically effective amount of the FAHFA or pharmaceutically acceptable salt thereof.

EXEMPLIFICATION

Example 1

Chronic 5- and 9-PAHSA treatment has no effect on total body weight and elevates serum 5- and 9-PAHSA and insulin levels in female non-obese diabetic (NOD) mice.
NOD Female Mice (Jackson Laboratory)
Age of mice at start of experiment: 4 weeks
Chow-fed: Diet 5008; housed 2 per cage
Route of Administration: Oral
Gavage—Once daily (between 11 AM and 1 PM)
Dose: 15 mg/kg body weight of each 5- and 9-PAHSA
Vehicle: 50% PEG400: 50% 1% Tween-80
Duration of treatment: 6 weeks Whether chronic 5- and 9-PHSA treatment in NOD mice enhances insulin secretion and whether these effects contribute to maintain glycemia during type 1 diabetes was tested. Chronic combined 5- and 9-PAHSA treatment by oral gavage in female NOD mice had no effect on body weight (FIG. 1A) or tissue mass (FIG. 1B). Serum 5- and 9-PAHSA levels were elevated 4-5 fold compared to vehicle-treated mice after 6 weeks of 5- and 9-PAHSA treatment (FIG. 1C). 5- and 9-PAHSA treatment augmented serum insulin levels after 6 weeks of treatment (FIG. 1D), and these effects were sustained for at least 13 weeks of PAHSA treatment. In addition, chronic 5- and 9-PAHSA treatment elevated serum CCL17 chemokine, a marker of alternatively activated macrophages, indicating that type 1 diabetes (T1D) protection elicited by PAHSAs may involve altered macrophage phenotypes from M1 to M2 (Padgett L E et al., Diabetes 2015). Furthermore, chronic combined 5- and 9-PAHSA treatment in female NOD mice had no toxic effects, as measured by serum alanine amino transferase (ALT) and creatinine levels and liver triglycerides (FIG. 1F).

Example 2

Chronic 5- and 9-PAHSA treatment attenuates percent cumulative diabetes incidence and improves percent survival in female NOD mice.
NOD Female Mice (Jackson Laboratory)
Age of mice at start of experiment: 4 weeks (FIGS. 2A to 2D); 13 weeks (late intervention study; FIG. 2E)
Chow-fed: Diet 5008; housed 2 per cage
Route of Administration: Oral
Gavage—Once daily (between 11 AM and 1 PM)
Dose: 15 mg/kg body weight of each 5- and 9-PAHSA
Vehicle: 50% PEG400: 50% 1% Tween-80
Duration of treatment: 26 weeks (FIGS. 2A to 2D); 13 weeks (late intervention study; FIG. 2E)

M1 macrophages play vital roles in the initiation of T1D, as human subjects and murine models display an early macrophage influx in the prediabetic stage. Whether chronic 5- and 9-PAHSA treatment in female NOD mice delays the onset of T1D, attenuates the cumulative diabetes incidence percent and improves survival rate was tested. Chronic 5- and 9-PAHSA treatment starting from 4 weeks of age significantly reduced the percent cumulative diabetes incidence by about 60% to 70% (FIGS. 2B and 2C) and improved the survival rate (FIG. 2D) without altering total body weight (FIG. 2A) compared to vehicle-treated mice. In addition, 5- and 9-PAHSA treatment starting from 13 weeks of age in the insulitis established NOD mice significantly reduced the percent cumulative diabetes incidence by about 60% and improved the survival rate (FIG. 2E) compared to the vehicle group.

In the late intervention study, the percent survival of mice was 54% for the vehicle-treated group (6 out of 13 mice died) and 85% for the PAHSA-treated group (2 out of 13 mice died).

Example 3

Chronic 5- and 9-PAHSA treatment attenuates insulitis score and percent intra-insulitis islets in female NOD mice.
NOD Female Mice (Jackson Laboratory)
Age of mice at start of experiment: 4 weeks
Chow-fed: Diet 5008; housed 2 per cage
Route of Administration: Oral
Gavage—Once daily (between 11 AM and 1 PM)
Dose: 15 mg/kg body weight of each 5- and 9-PAHSA
Vehicle: 50% PEG400: 50% 1% Tween-80
Duration of treatment: 6 weeks To determine whether insulitis was reduced by PAHSA treatment in female NOD mice, the degree of insulitis in the pancreas of vehicle and 5- and 9-PAHSA-treated NOD mice was evaluated. The mean insulitis score was significantly lower in prediabetic NOD mice treated with 5- and 9-PAHSA for 6 weeks compared to vehicle-treated NOD mice (FIG. 3A). The mean insulitis score was 0.48±0.07 in PAHSA-treated NOD mice compared to 0.73±0.1 in vehicle-treated NOD mice (n=16-17 mice per group, p=0.06).

In addition, mice treated with 5- and 9-PAHSA had the highest percentage of intact clear islets and significantly lower percentage of highly infiltrated intra-insulitis islets compared to vehicle-treated mice (FIG. 3B). PAHSAs had a subtle effect on the frequency of insulitis (no infiltration: vehicle 50±6 versus PAHSA 65±5% of islets) and on overall severity of insulitis (destructive insulitis: vehicle 23±5 versus PAHSA 13±2%) (FIG. 3B).

Example 4

PAHSAs augment percent viable pancreatic β-cells under cytokine stress in vitro.

Inflammatory cytokines such as interleukin 1β (IL-1β), tumor necrosis factor α (TNF-α) and interferon γ (INF-γ) induce pancreatic β-cell death in vitro. Whether PAHSAs protect pancreatic β-cell death during cytokine insult and augment percent viable β-cells was determined.

β-cell viability was studied using an MTT (3-(4,5-dimethylthiazol-2-yl)-2,5-diphenyl tetrazolium bromide) assay upon treatment of MIN6 cells with IL-1β in the presence of 5-PAHSA and 9-PAHSA. The MTT assay is a colorimetric assay that measures the reduction of yellow MTT by mitochondrial succinate dehydrogenase. MTT enters cells and passes into the mitochondria, where it is reduced to an insoluble, dark purple formazan product. The cells are then solubilized with an organic solvent (e.g., isopropanol) and the released, solubilized formazan reagent is measured spectrophotometrically. Reduction of MTT can occur only in metabolically active cells. Accordingly, absorbance of formazan produced is directly proportional to the number of viable cells.

In this experiment, MIN6 cells were grown to 70-80% confluence and treated with IL-1β (10 ng/mL) in the continuous presence or absence of 5-PAHSA (5 µM) and 9-PAHSA (5 µM) for 48 hours. At the end of the treatment period, MTT reagent (10 µL) was added to each well and cells were incubated for 2 additional hours. The formazan product formed was solubilized by adding MTT detergent (100 µL) and absorbance was measured at 570 nm.

Each treatment was performed in triplicate (n=3). The treatment groups were as follows: Treatment Group 1: IL-1β=10 ng/mL (reconstituted in phosphate-buffered saline (PBS)); Treatment Group 2: 5-PAHSA (5 µM (20 mM stock in DMSO)); Treatment Group 3: 9-PAHSA (5 µM (20 mM stock in DMSO)). FIG. 4A shows that clonal pancreatic β-cells, MIN6 cells, treated with IL-1β (10 ng/mL) for 48 hours induced β-cell death, and both 5-PAHSA and 9-PAHSA attenuated IL-1β induced cell death.

Percent viable β-cells was also determined using an MTT assay upon IL-1β and Cytomix treatment of MIN6 cells in the presence of 5-PAHSA and 9-PAHSA. Specifically, MIN6 cells were grown to 60-70% confluence and treated with IL-1β (10 ng/mL) and Cytomix in the continuous presence or absence of 5-PAHSA (5 µM) and 9-PAHSA (5 µM) for 40 hours. At the end of the treatment period, MTT reagent (10 µL) was added to each well and cells were incubated for 2 additional hours. The formazan product formed was solubilized by adding MTT detergent (100 µL) and absorbance was measured at 570 nm.

N=24 per treatment group. The treatment groups were as follows: Treatment Group 1: IL-1β=10 ng/mL (reconstituted in PBS); Treatment Group 2: Cytomix (TNF-α, IL-1β, IFN-γ; 10 ng/mL each); Treatment Group 3: 5-PAHSA (5 µM (20 mM stock in DMSO)); Treatment Group 4: 9-PAHSA (5 µM (20 mM stock in DMSO)). FIG. 4B shows that 5- and 9-PAHSA treatment increased the percent viable β-cells during inflammatory stress caused by either IL-1β alone or a mixture of cytokines IL-1β, TNF-α and IFN-γ.

Percent viable β-cells was determined using an MTT assay upon Cytomix treatment of MIN6 cells in the presence of 5-PAHSA and 9-PAHSA. Specifically, MIN6 cells were grown to 60-70% confluence and treated with Cytomix in the continuous presence or absence of 5-PAHSA (5 µM or 20 µM) or 9-PAHSA (5 µM or 20 µM) or 5- and 9-PAHSA (5 µM each) for 48 hours. At the end of the treatment period, MTT reagent (10 µL) was added to each well and cells were incubated for 2 additional hours. The formazan product formed was solubilized by adding MTT detergent (100 µL) and absorbance was measured at 570 nm. The amount of absorbance is directly proportional to number of viable cells N=30 per treatment group. The treatment groups were as follows: Treatment Group 1: Cytomix (5 ng/mL TNF-α, 5 ng/mL IL-1β, 10 ng/mL IFN-γ); Treatment Group 2: 5-PAHSA (5 µM or 20 µM (20 mM stock in DMSO)); Treatment Group 3: 9-PAHSA (5 µM or 20 µM (20 mM stock in DMSO)). FIG. 4C shows that 5- and 9-PAHSA treatment increased the percent viable β-cells during inflammatory stress caused by a mixture of cytokines IL-1β, TNF-α and IFN-γ.

Example 5

PAHSAs augment pancreatic β-cell proliferation during cytokine stress.

To determine whether the PAHSA-mediated increase in percent viable pancreatic β-cells was due to enhanced cell proliferation, MIN6 cells were tracked with CELLTRACE™ Violet and treated with either PAHSA alone or PAHSA and IL-1β. CELLTRACE™ Violet is a cell permeant, non-fluorescent ester of an amine-reactive fluorescent molecule, which enters cells by diffusion through the plasma membrane. Upon entry into the cell, the non-fluorescent molecule is converted by cellular esterases into a fluorescent derivative succinimidyl ester that covalently binds to amine groups in proteins, resulting in long-term dye retention within the cell. Through subsequent cell divisions, daughter cells receive approximately half of the fluorescent label of their parent cells, allowing the analysis of the fluorescence intensities of cells labeled and grown in vivo. Analysis of the level of fluorescence in the cell populations by flow cytometry permits the determination of the number of generations through which a cell has progressed since the label was applied and the calculation of the proliferation index.

In this experiment, MIN6 cells (0% confluence) were stained with cell tracer (CELLTRACE™ Violet, available from ThermoFisher) for 15 minutes and treated along with IL-1β in the presence or absence of 5-PAHSA or 9-PAHSA for 48 hours. At the end of the treatment period, cells were harvested and sorted by flow cytometry to determine β-cell proliferation index. Approximately 5,000 cells were sorted for each condition. The treatment groups were as follows: Treatment Group 1: IL-1β=10 ng/mL (reconstituted in PBS); Treatment Group 2: 5-PAHSA (5 µM or 20 µM (20 mM stock in DMSO)); Treatment Group 3: 9-PAHSA (5 µM or 20 µM (20 mM stock in DMSO).

Cells treated with IL-1β significantly attenuated β-cell proliferation, and both 5- and 9-PAHSA treatment augmented percent β-cell proliferation in control and IL-1β-treated cells (FIG. 5A).

To determine β-cell proliferation with Cytomix treatment in the presence of PAHSA, MIN6 cells were treated with Cytomix and diluent for 24 and 48 hours in the presence of 5- or 9-PAHSA in a bromodeoxyuridine (BrdU) proliferation assay. Specifically, MIN6 cells were grown to 60-70% confluence in a 96-well plate and treated with Cytomix (5 ng/mL TNF-α, 5 ng/mL IL-1β, 10 ng/mL IFN-γ) in the continuous presence or absence of 5-PAHSA (20 µM (20 mM stock in DMSO)) or 9-PAHSA (20 µM (20 mM stock in DMSO)) for 24 or 48 hours. N=10 per treatment. At the end of the treatment period, BrdU proliferation assay was performed according to the manufacturer's protocol. Absorbance was measured at 450 nm. The amount of absorbance is directly proportional to the number of proliferative β-cells.

FIGS. 5B and 5C show that the amount of BrdU incorporation into cells was significantly lowered in Cytomix-treated cells compared to control, and both 5- and 9-PAHSA enhanced BrdU incorporation into the cells during Cytomix insult. Together, these data indicate that both 5- and 9-PAHSA enhance β-cell proliferation in vitro and augment percent viable β-cells during cytokine stress.

Example 6

PAHSAs attenuate cytokine-induced apoptotic and necrotic β-cells in vitro.

To determine whether PAHSAs attenuate cytokine-induced apoptotic and necrotic β-cell death, MIN6 cells were treated with Cytomix in continuous presence or absence of 5- or 9-PAHSA. Specifically, MIN6 cells were grown to 60-70% confluence and treated with Cytomix in the continuous presence or absence of 5-PAHSA (20 µM), and 9-PAHSA (20 µM) for 24 hours. At the end of the treatment, cells were stained with Annexin V and PI for 15 minutes and flow cytometry was performed to evaluate the number of Annexin V and PI positive cells. The number of Annexin V and PI positive stained cells reflects the number of apoptotic beta cells.

Annexin V binds to phosphatidylserine (PS). In normal viable cells, PS is located on the cytoplasmic surface of the cell membrane. In the intermediate stage of apoptosis, PS translocates from the inner to the outer leaflet of the membrane, exposing PS to the external cellular environment. Fluorescent annexin V conjugates are used to detect the externalization of PS. PI is an intercalating agent and a fluorescent molecule. PI is used as a DNA stain for both flow cytometry to evaluate cell viability or DNA content in cell cycle analysis. Annexin V and PI positive staining represents late apoptotic or necrotic cells.

N=6 per treatment group. The treatment groups were as follows: Treatment Group 1: Cytomix (5 ng/mL TNF-α, 5 ng/mL IL1β, 10 ng/mL IFN-γ); Treatment Group 2: 5-PAHSA (20 µM (20 mM stock in DMSO)); Treatment Group 3: 9-PAHSA (20 µM (20 mM stock in DMSO)).

Cytomix treatment decreased the percent viable β-cell and increased the percent apoptotic and necrotic cells measured by Annexin V and PI staining (FIGS. 6A-C). Both 5- and 9-PAHSA significantly attenuated Cytomix-induced apoptotic and necrotic β-cell death and increased percent viable β-cells (FIGS. 6A-C). Therefore, 5- and 9-PAHSA promote β-cell survival during cytokine insult by attenuating apoptotic and necrotic cell death.

Example 7

PAHSAs attenuate pancreatic β-cell death in vitro by inhibiting caspase-3 degradation and endoplasmic reticulum stress.

It is well-established that cytokine-mediated pancreatic β-cell death is mediated via caspase-3 activation. In addition, it has been shown that cytokines trigger the endoplasmic reticulum stress leading to caspase-3 activation and, ultimately, β-cell death. Therefore, whether protective effects of PAHSAs on cytokine-induced β-cell death are mediated by attenuating endoplasmic reticulum stress and caspase-3 cleavage was investigated. Specifically, MIN6 cells were grown to 60-70% confluence and treated with Cytomix (5 ng/mL TNF-α, 5 ng/mL IL-1β, 10 ng/mL IFN-γ) for 24 hours or thapsigargin (2 µmol/L) for 6 hours in the continuous presence or absence of 5-PAHSA (20 µM (20 mM stock in DMSO)) or 9-PAHSA (20 µM (20 mM stock in DMSO)). N=4-6 per treatment group. At the end of the treatment, cells were collected and Western blots were performed for caspase-3 and PARP cleavage.

Cytomix treatment increased caspase-3 cleavage in clonal pancreatic β-cells, as measured by a decrease in pro-caspase 3, and both 5- and 9-PAHSA significantly attenuated cleaved caspase-3 (FIG. 7A). In addition, thapsigargin induced endoplasmic reticulum stress in MIN6 cells by increasing PARP cleavage, and only 5-PAHSA but not 9-PAHSA attenuated PARP cleavage in MIN6 cells in presence of thapsigargin (FIG. 7B). Taken together, these data show that PAHSAs attentuate cytokine-induced pancreatic β-cell death by attenuating caspase-3 cleavage and endoplasmic reticulum stress.

Example 8

PAHSAs augment glucose-stimulated insulin secretion during cytokine-induced β-cell distress.

Cytokines have been implicated as immunological effector molecules that attenuate insulin secretion from pancreatic β-cells in addition to causing β-cell destruction. It was observed that PAHSAs attenuated cytokine-mediated β-cell death, so whether PAHSAs augment glucose-stimulated insulin secretion during cytokine-mediated β-cell distress was also evaluated. Specifically, MIN6 cells were grown to 70% confluence and treated with Cytomix (5 ng/mL TNF-α, 5 ng/mL IL-1β, 10 ng/mL IFN-γ) in the continuous presence or absence of 5-PAHSA (20 µM (20 mM stock in DMSO)) or 9-PAHSA (20 µM (20 mM stock in DMSO)) for 24 hours. At the end of the treatment, cells were incubated with Krebs-Ringer Bicarbonate (KRB) buffer for 3 hours and stimulated with 2.5 mM glucose (low glucose) and 20 mM glucose (high glucose) for 45 minutes. At the end of the incubation, 100 mL of KRB was collected to measure insulin release by ELISA.

MIN6 cells treated with Cytomix for 24 hours displayed a decrease in insulin secretion at both low (2.5 mM) and high (20 mM) glucose concentrations. Both 5- and 9-PAHSA treatment in presence of Cytomix augmented glucose-stimulated insulin secretion in MIN6 cells compared to Cytomix alone (FIG. 8). Together, these data suggest that PAHSAs potentiate glucose stimulated insulin secretion by attenuating β-cell death and augmenting β-cell proliferation during cytokine insult.

Example 9

PAHSA levels in human islets.

Using targeted mass spectrometry analysis, 13/12-, 10- and 9-PAHSA isomers have been identified in isolated healthy human islets. 9-PAHSA was the predominant isomer in the human islets and the levels of 13/12- and 10-PAHSA were similar. Lipids were extracted from approximately 5,000 islet equivalents (IEQs).

Example 10

Chronic 5- and 9-PAHSA treatment maintains serum insulin levels in female NOD mice.
NOD Female Mice (Jackson Laboratory)
Age of mice at start of experiment: 3.5 weeks
Chow-fed: Diet 5008; housed 2 per cage
Route of Administration: Oral
Gavage—Once daily (between 11 AM and 1 PM)
Dose: 15 mg/kg body weight of each 5- and 9-PAHSA
Vehicle: 50% PEG400: 50% 1% Tween-80
Duration of treatment: 18 weeks
N=9 mice/treatment group. After 18 weeks of treatment, one vehicle- and one PAHSA-treated mouse had died. The vehicle-treated mouse died just prior to 18 weeks of age, while the PAHSA-treated mouse died just after attaining 20 weeks of age. The cumulative diabetes incidence of vehicle treatment at the end of the treatment period was 67% (6 out of 9 vehicle-treated mice had diabetes, while the cumulative diabetes incidence of PAHSA treatment at the end of the treatment period was 22% (2 out of 9 PAHSA-treated mice had diabetes). Body weight of mice was unaffected by 18 weeks of gavage with 5- and 9-PAHSA compared to vehicle-treated mice. Tables 1 and 2 show that serum insulin levels were maintained in more NOD mice gavaged with 5- and 9-PAHSA than with vehicle.

TABLE 1

5- & 9-PAHSA gavage (15 mg/kg each) - 17 wk. Treatment

| Mouse ID | Glycemia (mg/dL) | Insulin (ng/mL) |
| --- | --- | --- |
| P1 | 136 | 0.53 |
| P2 | 100 | 1.09 |
| P3 | 125 | 0.44 |
| P4 | 134 | 0.4 |
| P5 | DEAD | |
| P6 | 127 | Serum Problem |
| P7 | 117 | 0.5 |
| P8 | 539 | Below Range |
| P9 | 165 | 0.5 |

TABLE 2

Vehicle gavage - 17 wk. Treatment

| Mouse ID | Glycemia (mg/dL) | Insulin (ng/mL) |
| --- | --- | --- |
| V1 | 167 | 0.57 |
| V2 | DEAD | |
| V3 | HG (>600) | Below Range |
| V4 | 112 | 0.44 |
| V5 | 550 | Below Range |
| V6 | 129 | 0.64 |
| V7 | HG (>600) | Below Range |
| V8 | HG (>600) | Below Range |
| V9 | 456 | Below Range |

Example 11

Chronic 5- and 9-PAHSA treatment has minimal effect on insulitis but reduces pancreatic T-cell activation in NOD mice.

Figure 9B:
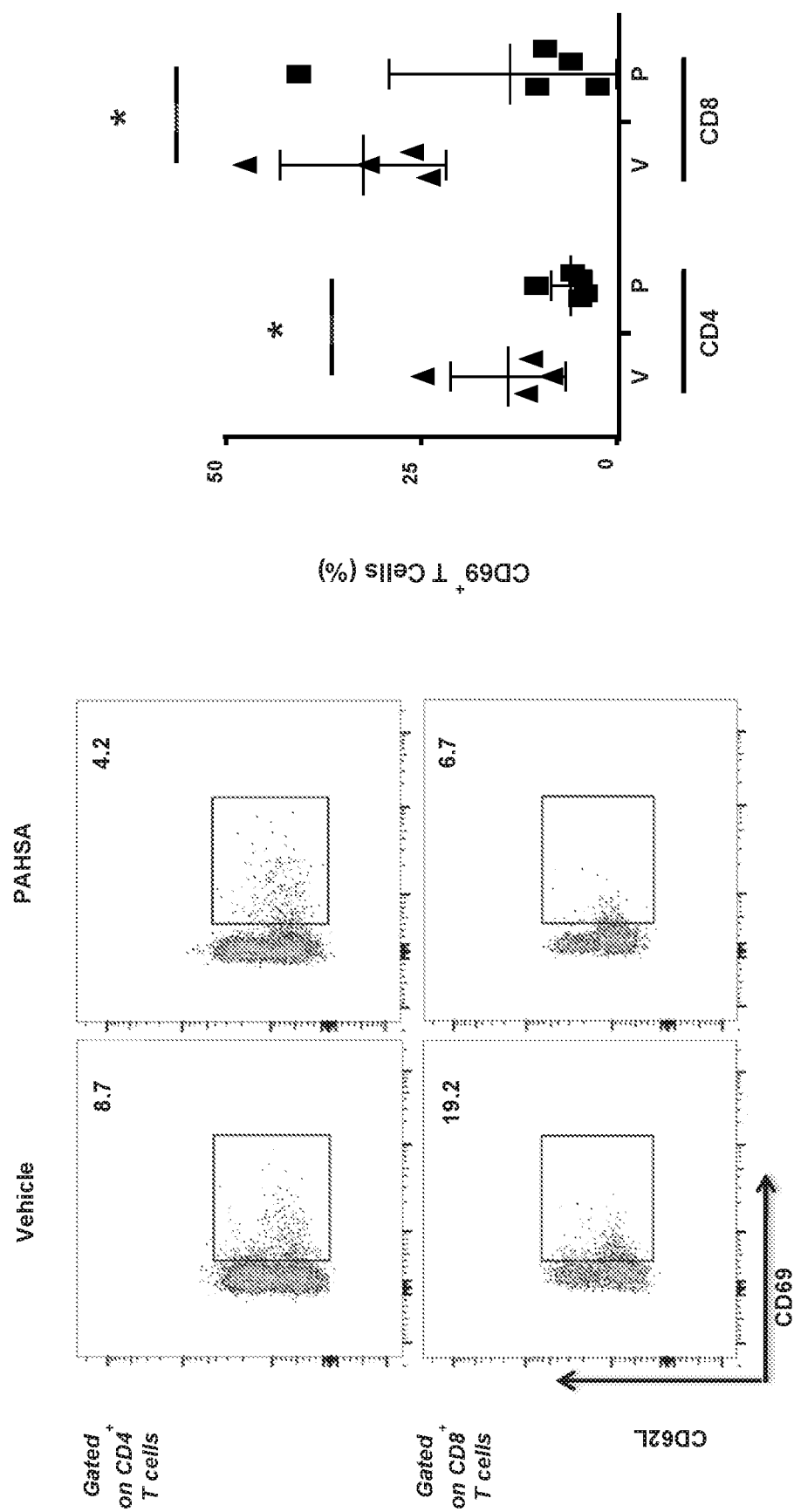
Figure 9C:
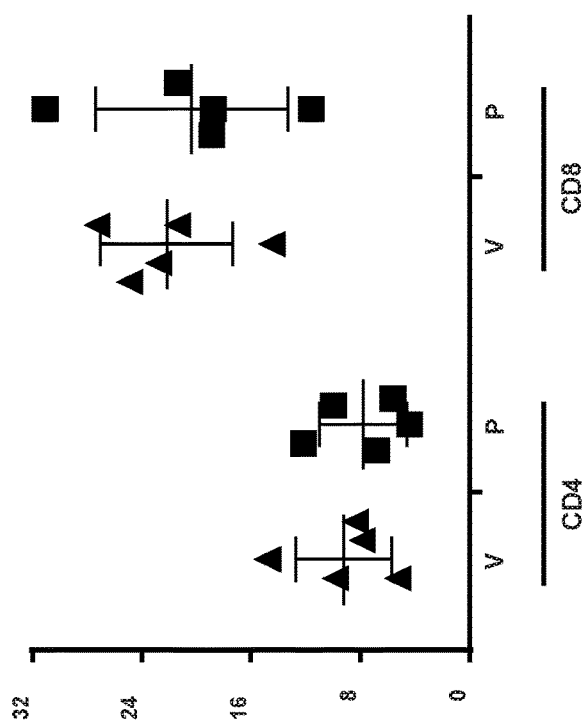
Figure 9C:
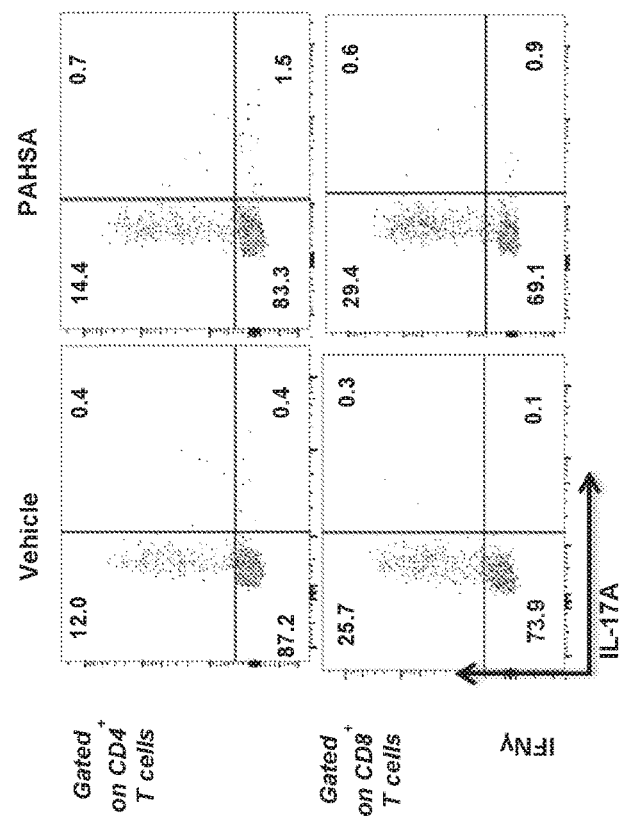

To determine the mechanism(s) by which PAHSAs attenuate T1D in NOD mice, the effects of PAHSA treatment on inflammatory immune markers were examined. Flow cytometric analysis of the pancreatic infiltrate with 7 weeks of PAHSA treatment (11 weeks of age) showed a similar number of leukocytes (CD45$^+$ cells) compared to vehicle-treated mice (FIG. 9A; left panel). At 15 weeks of age, vehicle treatment increased leukocyte infiltration by 2-fold. However, PAHSA treatment prevented this increase (FIG. 9A; right panel). Furthermore, PAHSA treatment for 11 weeks showed a concomitant reduction in acute T-cell activation, as measured by CD69 expression (FIG. 9B; left panel—gating strategy). Population of other T-cell activation markers, interferon-γ (INF-γ) (FIG. 9C; left panel—gating strategy) and programmed cell death protein-1 (PD-1) (FIG. 10C), were unaltered with PAHSA treatment. The reduction in total number of pancreatic-infiltrating cells in PAHSA-treated mice held true for nearly all populations examined, but the fractional representation of pancreatic-infiltrating cells within the bulk CD45$^+$ compartment appeared to be unaltered in PAHSA-versus vehicle-treated mice (FIGS. 10A and 10B). However, the percent B-cells was significantly lowered with PAHSA treatment compared to vehicle treatment (FIG. 10B). In addition, PAHSA treatment did not alter the percent of Foxp3$^+$ CD4$^+$ T-cells (T$_{regs}$) (FIG. 9F; left panel—gating strategy), but increased Foxp3 protein levels in pancreatic T$_{regs}$ (FIG. 9G). Overall Foxp3 expression levels have been shown to correlate with suppressive capacity of T$_{regs}$, so it is intriguing to speculate that T$_{regs}$ from PAHSA-treated mice may have greater suppressive qualities. Together, these data suggest that chronic PAHSA treatment delays T1D onset and reduces its incidence in NOD mice by attenuating leukocyte infiltration and T-cell activation.

Example 12

PAHSA treatment increases islet β-cell proliferation under cytokine stress in vivo.

Figure 11A:
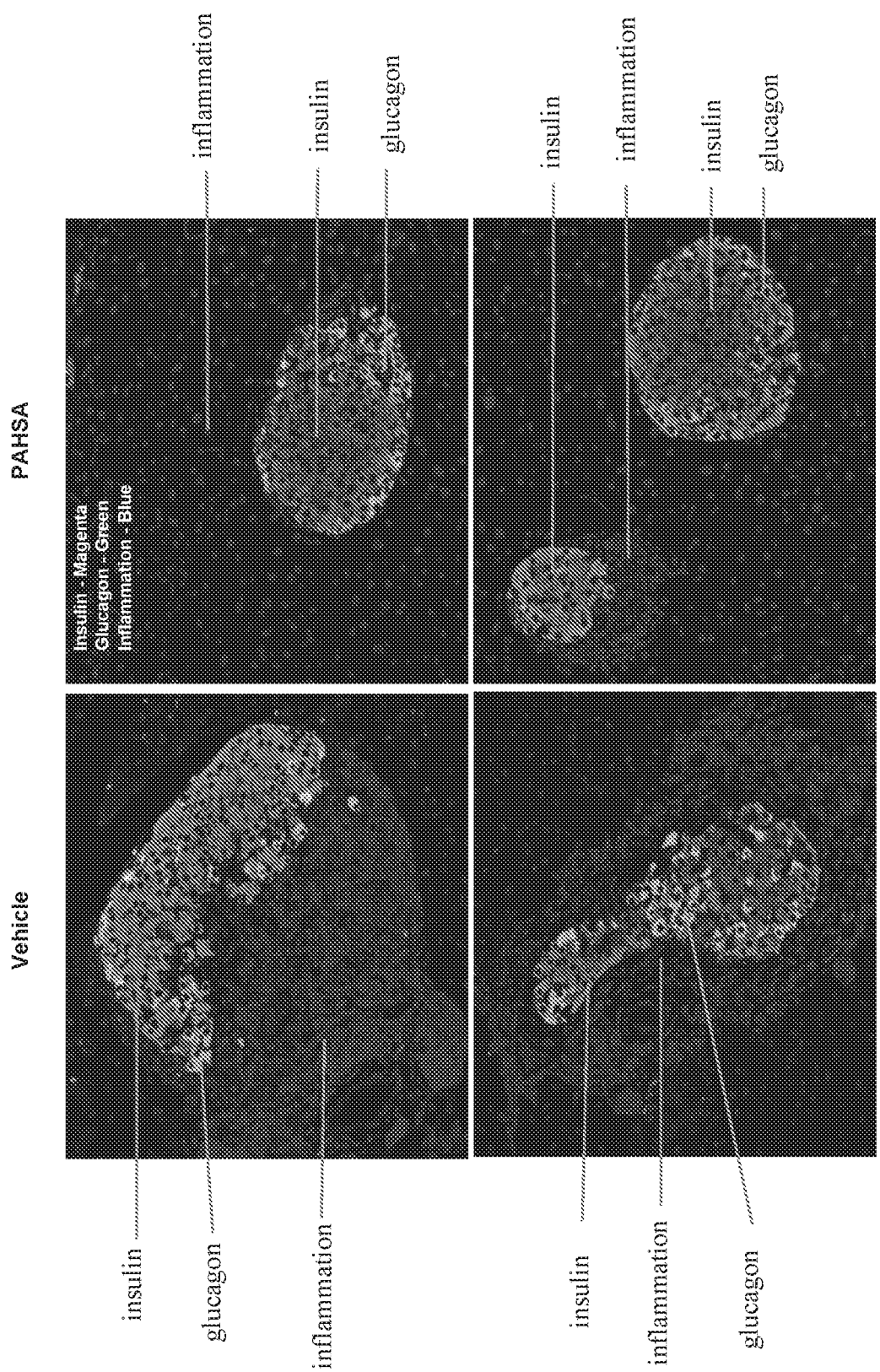

It was determined whether PAHSAs increase pancreatic β-cell proliferation during cytokine insult. PAHSA treatment for 6 weeks starting from 4 weeks of age attenuated inflammation resulting in maintenance of islet architecture and less islet expansion (FIG. 11A). Vehicle-treated mice showed enlargement of islets and loss of normal islet architecture due to infiltration with immune cells. This was associated with greater relative β-cell mass per islet with no change in α-cell relative mass compared to vehicle-treated mice (FIG. 11B). This appears to be due to β-cell proliferation in PAHSA-treated mice, since islets from PAHSA-treated mice showed an increase in the percent of insulin positive cells which are also positive for Ki67 compared to vehicle-treated mice (FIG. 11C). This did not appear to be a generalized effect, since liver from PAHSA-treated mice did not show an increase in Ki67-positive cells (FIG. 11D).

Example 13

PAHSAs augment glucose-stimulated insulin secretion during cytokine-induced β-cell distress.

Cytokines attenuate insulin secretion from pancreatic β-cells in addition to causing β-cell destruction. It was determined whether PAHSAs augment glucose-stimulated insulin secretion (GSIS) during cytokine-mediated β-cell distress. Cytomix treatment decreased insulin secretion at both low (2.5 mM) and high (20 mM) glucose concentrations in human islets (FIG. 12). PAHSAs partially blocked the ability of Cytomix to reduce GSIS at high glucose but not low glucose concentrations in human islets (FIG. 12). Together, these data suggest that PAHSAs potentiate GSIS by attenuating β-cell death and augmenting β-cell proliferation during cytokine insult.

REFERENCES

Yore, M. M., Syed, I., Moraes-Vieira, P. M., Zhang, T., Herman, M. A., Homan, E. A., Patel, R. T., Lee, J., Chen, S., Peroni, O. D., Dhaneshwar, A. S., Hammarstedt, A., Smith, U., McGraw, T. E., Saghatelian, A., Kahn, B. B. Discovery of a class of endogenous mammalian lipids with anti-diabetic and anti-inflammatory effects. Cell 2014; 159 (2): 318-332.

Padgett, L. E., Burg, A. R., Lei, W. and Tse, H. M. Loss of NADPH Oxidase-Derived Superoxide Skews Macrophage Phenotypes to Delay Type 1 Diabetes. Diabetes 2015; 64: 937-946.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for treating type 1 diabetes in a subject in need thereof, comprising administering to the subject a therapeutically effective amount of a fatty acid ester of a hydroxy fatty acid (FAHFA), or a pharmaceutically acceptable salt thereof.

2. The method of claim 1, wherein the FAHFA is represented by the following structural formula:

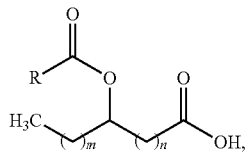

or a pharmaceutically acceptable salt thereof, wherein:
R is an aliphatic group;
m is an integer from 0 to 21;
n is an integer from 0 to 21; and
the sum of m and n is an integer from 11 to 21.

3. The method of claim 2, wherein R is a $C_1$-$C_{20}$ aliphatic group.

4. The method of claim 3, wherein R is a $C_{15}$-$C_{20}$ aliphatic group.

5. The method of claim 4, wherein R is a $C_{15}$, $C_{16}$ or $C_{17}$ aliphatic group.

6. The method of claim 2, wherein R is an alkyl group.

7. The method of claim 1, wherein the FAHFA is a palmitoleic acid ester of hydroxy palmitoleic acid (POHPO), a palmitic acid ester of hydroxy palmitoleic acid (PAHPO), an oleic acid ester of hydroxy palmitoleic acid (OAHPO), a stearic acid ester of hydroxy palmitoleic acid (SAHPO), a palmitoleic acid ester of hydroxy palmitic acid (POHPA), a palmitic acid ester of hydroxy palmitic acid (PAHPA), an oleic acid ester of hydroxy palmitic acid (OAHPA), a stearic acid ester of hydroxy palmitic acid (SAHPA), a palmitoleic acid ester of hydroxy oleic acid (POHOA), a palmitic acid ester of hydroxy oleic acid (PAHOA), an oleic acid ester of hydroxy oleic acid (OAHOA), a stearic acid ester of hydroxy oleic acid (SAHOA), a palmitoleic acid ester of hydroxy stearic acid (POHSA), a palmitic acid ester of hydroxy stearic acid (PAHSA), an oleic acid ester of hydroxy stearic acid (OAHSA) or a stearic acid ester of hydroxy stearic acid (PAHSA), a stereoisomer of any of the foregoing, a pharmaceutically acceptable salt of any of the foregoing, or a combination of any of the foregoing.

8. The method of claim 7, wherein the FAHFA is a palmitic acid ester of hydroxy stearic acid (PAHSA), or a pharmaceutically acceptable salt thereof.

9. The method of claim 8, wherein the PAHSA is O-palmitoyl-5-hydroxystearic acid (5-PAHSA), O-palmitoyl-7-hydroxystearic acid (7-PAHSA), O-palmitoyl-8-hydroxystearic acid (8-PAHSA), O-palmitoyl-9-hydroxystearic acid (9-PAHSA), 0-palmitoyl-10-hydroxystearic acid (10-PAHSA), O-palmitoyl-11-hydroxystearic acid (11-PAHSA) or O-palmitoyl-12/13-hydroxystearic acid (12/13-PAHSA), a pharmaceutically acceptable salt of any of the foregoing, or a combination of any of the foregoing.

10. The method of claim 9, wherein the PAHSA is O-palmitoyl-5-hydroxystearic acid (5-PAHSA) or O-palmitoyl-9-hydroxystearic acid (9-PAHSA), a pharmaceutically acceptable salt of any of the foregoing or a combination of any of the foregoing.

11. The method of claim 1, wherein the FAHFA, or the pharmaceutically acceptable salt thereof, is administered in combination with a second FAHFA, or a pharmaceutically acceptable salt thereof.

* * * * *